United States Patent
Roy et al.

(10) Patent No.: US 11,560,414 B2
(45) Date of Patent: Jan. 24, 2023

(54) KITS COMPRISING MYOKINES AND PLATINUM-BASED CHEMOTHERAPEUTIC AGENTS FOR TREATING COLORECTAL CANCER

(71) Applicant: Northwestern University, Evanston, IL (US)

(72) Inventors: Hemant K. Roy, Chestnut Hill, MA (US); Vadim Backman, Chicago, IL (US)

(73) Assignee: Northwestern University, Evanston, IL (US)

( * ) Notice: Subject to any disclaimer, the term of this patent is extended or adjusted under 35 U.S.C. 154(b) by 6 days.

(21) Appl. No.: 16/877,275

(22) Filed: May 18, 2020

(65) Prior Publication Data

US 2020/0362001 A1  Nov. 19, 2020

Related U.S. Application Data

(60) Provisional application No. 62/848,914, filed on May 16, 2019, provisional application No. 62/850,526, filed on May 20, 2019.

(51) Int. Cl.

| | |
|---|---|
| *A61K 38/18* | (2006.01) |
| *A61K 38/00* | (2006.01) |
| *A61P 35/00* | (2006.01) |
| *A61P 3/10* | (2006.01) |
| *A61P 9/00* | (2006.01) |
| *C07K 14/47* | (2006.01) |
| *C07K 14/52* | (2006.01) |
| *C07K 14/475* | (2006.01) |
| *A61K 31/282* | (2006.01) |

(52) U.S. Cl.
CPC .......... *C07K 14/475* (2013.01); *A61K 31/282* (2013.01); *C07K 14/4703* (2013.01); *A61K 38/00* (2013.01)

(58) Field of Classification Search
CPC ...... A61K 31/282; A61K 38/00; A61K 38/18; A61P 35/00; A61P 3/10; A61P 9/00; C07K 14/4703; C07K 14/475; C07K 14/52; C07K 14/47
See application file for complete search history.

(56) References Cited

U.S. PATENT DOCUMENTS

| | | | |
|---|---|---|---|
| 5,595,756 A * | 1/1997 | Bally ................... | A61K 9/1272 264/4.1 |
| 2017/0290882 A1* | 10/2017 | Andronova .......... | A61K 31/711 |
| 2017/0360955 A1* | 12/2017 | Janssen ............... | A61K 47/6849 |
| 2019/0142900 A1 | 5/2019 | Roy | |

OTHER PUBLICATIONS

Rodgers et al., "Isolation and Characterization of Myostatin Complementary Deoxyribonucleic Acid Clones from Two Commercially Important Fish: Oreochromis mossambicus and Morone chrysops," Endocrinology, 2001, 142(4): 1412-1418. (Year: 2001).*
Zheng et al., "Metrnl: a secreted protein with new emerging functions," Acta Pharmacologica Sinica, 2016, 37: 571-579. (Year: 2016).*
Langley et al., "Myostatin inhibits rhabdomyosarcoma cell proliferation through an Rb-independent pathway," Oncogene, 2004, 23: 524-534. (Year: 2004).*
Comella et al., Role of oxaliplatin in the treatment of colorectal cancer, Therapeutics and Clinical Risk Management, 2009, 5: 229-238. (Year: 2009).*
Intro to Cancer from Merck Manual, p. 1. Accessed Mar. 5, 2008. (Year: 2008).*
Overview of Brain Tumors from Merck Manual, pp. 1-6. Accessed Jan. 13, 2022. (Year: 2022).*
Overview of Leukemia from Merck Manual, pp. 1-2. Accessed Jan. 13, 2022. (Year: 2022).*
Colorectal Cancer from Merck Manual, pp. 1-6. Accessed Jan. 13, 2022. (Year: 2022).*
Prostate Cancer from Merck Manual, pp. 1-8. Accessed Jan. 13, 2022. (Year: 2022).*
Breast Cancer from Merck Manual, pp. 1-25. Accessed Jan. 13, 2022. (Year: 2022).*
Sporn et al., "Chemoprevention of cancer," Carcinogenesis, 2000, 21(3): 525-530. (Year: 2000).*
Auerbach et al., "Angiogenesis assays: Problems and pitfalls," Cancer and Metastasis Reviews, 2000, 19: 167-172. (Year: 2000).*
Gura, Trisha, "Systems for Identifying New Drugs Are Often Faulty," Science, 1997, 278: 1041-1042. (Year: 1997).*
Gravanis et al., "The changing world of cancer drug development: the regulatory bodies' perspective," Chinese Clinical Oncology, 2014, 3(2): 1-5. (Year: 2014).*
Hait, WN., "Anticancer drug development: the grand challenges," Nature Reviews, 2010, 9: 253-254. (Year: 2010).*

* cited by examiner

*Primary Examiner* — Julie Ha
(74) *Attorney, Agent, or Firm* — Quarles & Brady LLP

(57) ABSTRACT

Disclosed are compositions comprising myokines and their methods of preparation and use. The disclosed myokine compositions and methods may comprise myokines having a molecular weight of greater than about 10 kDa such as myostatin and metrnl. The disclosed myokine compositions and methods may be utilized for treating and/or preventing cell proliferative and metabolic diseases and disorders. In particular, the disclosed myokine compositions and methods may be utilized for treating and/or preventing cell proliferative and metabolic diseases and disorders, such as cancer, and metabolic diseases and disorders, such as diabetes, non-alcoholic fatty liver disease, and heart disease.

9 Claims, 37 Drawing Sheets

(a)

| Drug | Class | Date/Company | Indications | Toxicity, off target effects |
|---|---|---|---|---|
| Cetuximab (Erbitux) | mAb | 2/2004 (BMS) | Metastatic CRC, HNSCC | Infusion Rx (part mouse) |
| Erlotinib (tarceva) | TKI | 11/2004 (OSI) | NSCLC, pancreatic ca | ILD/liver tox |
| Gefitinib (Iressa) | TKI | 5/2003 (Astra-Z) | NSCLC | ILD/liver tox |
| Lapatinib (Tykerb) | TKI | 3/2007 (SKB) | Metastatic breast ca | Also targets Her2 |

KITS COMPRISING MYOKINES AND PLATINUM-BASED CHEMOTHERAPEUTIC AGENTS FOR TREATING COLORECTAL CANCER

CROSS-REFERENCE TO RELATED PATENT APPLICATIONS

The present application claims the benefit of priority under 35 U.S.C. § 119(e), to U.S. Provisional Application No. 62/848,914, filed on May 16, 2019, and U.S. Provisional Application No. 62/850,526 filed on May 20, 2019, the contents of which are incorporated herein by reference in their entireties.

STATEMENT REGARDING FEDERALLY SPONSORED RESEARCH OR DEVELOPMENT

This invention was made with government support under EFMA-1830961 awarded by the National Science Foundation and CA228272 awarded by the National Institutes of Health. The government has certain rights in the invention.

BACKGROUND

The field of the invention relates to the identification and use of myokines for treating and/or preventing cell proliferative and metabolic diseases and disorders. In particular, the field of the invention relates to the use of myokines for treating and/or preventing cell proliferative and metabolic diseases and disorders, such as cancer, and metabolic diseases and disorders, such as diabetes, non-alcoholic fatty liver disease, and heart disease.

Physical activity has numerous beneficial health effects and is an important health behavior for the prevention and management of a myriad of human diseases. In particular, exercise has been shown to reduce the risk of developing some cancers, help cancer survivors cope with and recover from treatments, improve the long-term health of cancer survivors, and even reduce the risk of recurrence in some groups. Exercise also is known to be beneficial for subjects having or at risk for developing metabolic disorders. However, the mechanism of action remains unknown.

Here, the inventors disclose methods for preparing and isolating myokines from stimulated myotubules. The inventors have shown that myokines thus prepared and isolated can be utilized for treating diseases and disorders such as cell proliferative diseases and disorders. Further, the inventors have identified particular myokines that can be useful for treating cell proliferative diseases and disorders. The inventors' findings have implications for treating cancer and metabolic diseases and disorders.

SUMMARY

Discloses are myokines, compositions comprising myokines, methods for preparing and isolating myokines, and methods of using myokines for treating and/or preventing cell proliferative and metabolic diseases and disorders. In particular, the disclosed myokines and compositions may be administered for treating and/or preventing cell proliferative and metabolic diseases and disorders, such as cancer, and metabolic diseases and disorders, such as diabetes, non-alcoholic fatty liver disease, and heart disease.

BRIEF DESCRIPTION OF THE FIGURES

FIG. 8. Chemotherapeutic drugs that target EGFR, indications, and toxicity.

DETAILED DESCRIPTION

Figure 1:
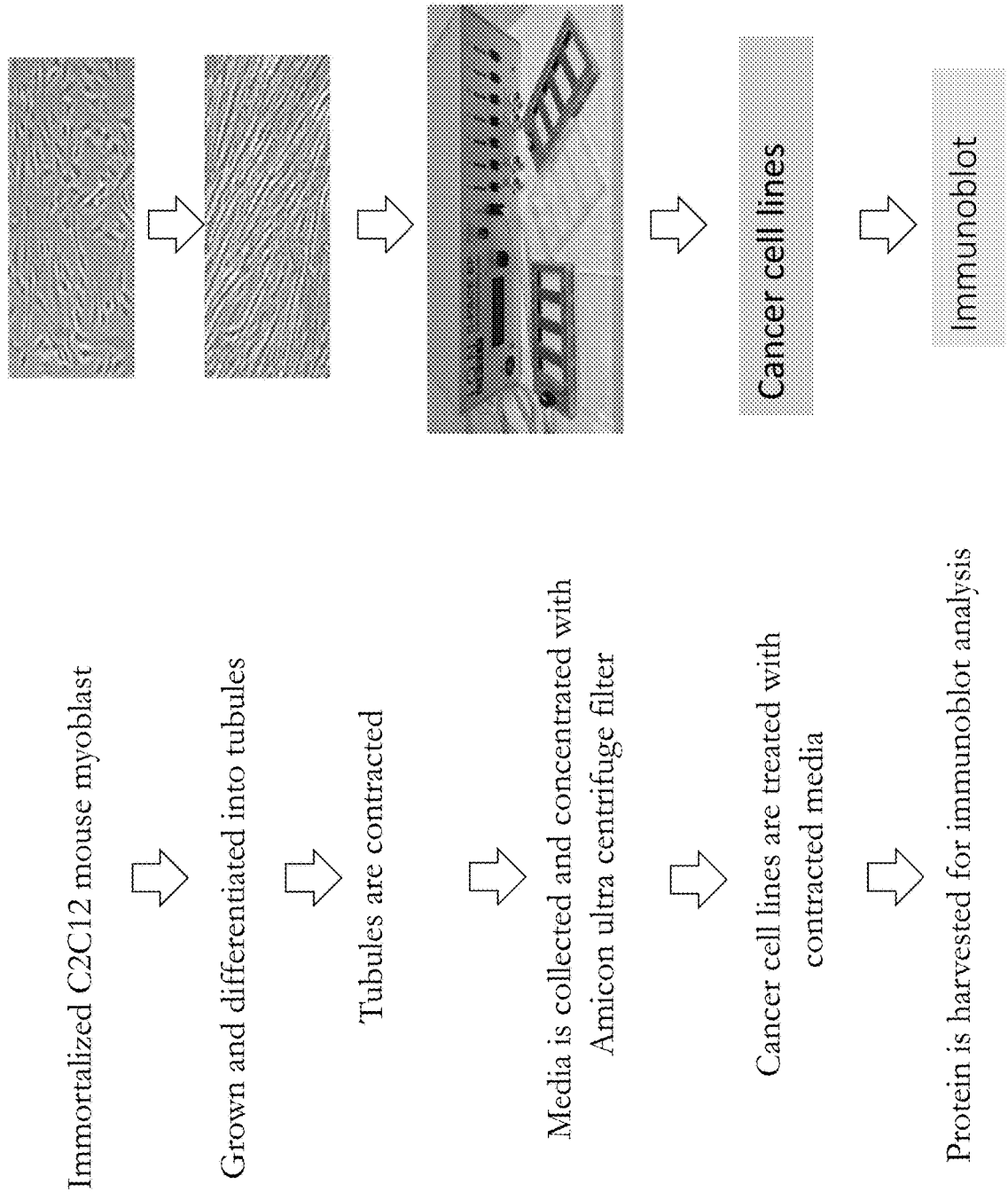
FIG. 1. General description of the myokine generation platform. Contractile cells are exposed to a variable current that makes them contract. Contracting cells synthesize about 3000 myokines.

The disclosed subject matter relates to myokines, compositions comprising myokines, methods for preparing and isolating myokines, and methods of using myokines for treating and/or preventing cell proliferative and metabolic diseases and disorders. The disclosed subject matter may be described using terms and definitions as follows.

As used in this specification and the claims, the singular forms "a," "an," and "the" include plural forms unless the context clearly dictates otherwise. For example, the term "a myokine" or "a therapeutic agent" should be interpreted to mean "one or more myokines" and "one or more therapeutic agents," respectively, unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

The term "cryopreservative" generally includes agents which provide stability to a composition against freezing stresses, presumably by being preferentially excluded from the surface. Cryopreservatives also may offer protection during long-term product storage. Examples of cryopreservatives may include, but are not limited to, polymers (such as dextran and polyethylene glycol; sugars such as sucrose, glucose, trehalose, and lactose), surfactants (such as polysorbates), and amino acids (such as glycine, arginine, and serine).

As used herein the terms "culture media" and "culture medium" are used interchangeably and refer to a solid or a liquid substance used to support the growth of cells (e.g., myotubules). Preferably, the culture media as used herein refers to a liquid substance capable of maintaining myotubules. The culture media can be a water-based media which includes a combination of ingredients such as salts, nutrients, minerals, vitamins, amino acids, nucleic acids, proteins such as cytokines, growth factors and hormones, all of which are needed for cell proliferation and are capable of maintaining stem cells in an undifferentiated state. For example, a culture media can be a synthetic basal media supplemented with the necessary additives. Preferably, all ingredients included in the culture media of the present disclosure are substantially pure and tissue culture grade.

An "effective amount" is an amount of a composition or component (e.g., stimulated muscle medium or myokines) sufficient to effect beneficial or desired results. An effective amount can be in one or more administrations, applications or dosages.

The term "electrical pulse stimulation" (EPS) refers to the use of an electric current to stimulate a cell, for example, to stimulate contraction of a muscle cell. Electrical impulses are generated by any device known to one of skill in the art and delivered through electrode probes in proximity to the cells to be stimulated. The impulses can mimic the action potential coming from the central nervous system that cause muscle cells to contract.

The term "fractionating" as used herein refers to the process of dividing the stimulated muscle medium into smaller sub-portions or fractions on the basis of some physical, chemical or biochemical property and using any technique known of one skilled in the art. Non-limiting examples of some fractionating techniques include, but are not limited to column chromatography, HPLC, FPLC, matrix-affinity chromatography, reverse-phase chromatography, and electrophoretic separation.

Suitable cells for the disclosed methods may include, but are not limited to, cells derived or differentiated from myoblasts. In some embodiments, suitable cells for the disclosed methods may include muscle cells (e.g., muscle cells that have been differentiated from myoblasts). In some embodiments, suitable cells for the disclosed methods may include myotubule cells (e.g., myotubule cells that have been differentiated from myoblasts).

As used herein, the term "myokine" refers to peptides or polypeptides, bioactive lipids, second messengers, etc. derived from muscle cells. The term "muscle cells" refers to those cells making up contractile tissue of animals. Muscle cells are derived from the mesodermal layer of embryonic germ cells. Muscle cells contain contractile filaments that move past each other and change the size of the cell. Muscle cells may be classified as skeletal, cardiac, or smooth muscles.

The term "therapeutic" as used herein in reference to treatment of cancer means any therapeutically useful agent and/or procedure for the treatment, remission or attenuation of a disease state, physiological condition, symptoms, or etiological factors, or for the evaluation or diagnosis thereof. A therapeutic agent may be a chemotherapeutic agent, for example, mitotic inhibitors, topoisomerase inhibitors, steroids, anti-tumor antibiotics, antimetabolites, alkylating agents, enzymes, proteasome inhibitors, any combinations thereof, and the like.

The term "treating" or "treatment" covers the treatment of a disease or disorder (e.g., cancer), in a subject and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, "treating" or "treatment" refers to the killing of cancer cells. The term "kill" with respect to a cancer treatment is directed to include any type of manipulation that will lead to the death of that cancer cell or at least a portion of a population of cancer cells.

Myokines for Treating Cell Proliferative and Metabolic Diseases and Disorders

In some aspects provided herein are in vitro methods for generating myokines comprising: (a) exposing myotubules in a culture medium to electrical pulse stimulation (EPS) conditions for a period of time to generate stimulated muscle medium; and (b) separating the stimulated muscle medium from at least a portion of the myotubules. The methods disclosed herein may be performed by practicing one or methods as disclosed in U.S. Published Application No. 2019/0142900, published May 16, 2018, the content of which is incorporated herein by reference in its entirety.

In the disclosed methods, cells such as myotubule cells may be subjected to EPS conditions for a suitable length of time. Suitable lengths of time may include at least about 0.5, 1, 2, 3, 4, 5, 6, 7, 8, 9, 10, 11, 12, 13, 14, 15, 16, 17, 18, 19, 20, 21, 22, 23, or 24 or for a length of time within a range bounded by any of these values, e.g., 5-10 hours.

In the disclosed methods, cells such as myotubule cells may be subjected to EPS conditions having a suitable electrical potential. Suitable electrical potentials may include, but are not limited to, at least about 10, 15, 20, 35, 30, 35, 40, 45, or 50 volts, or an electrical potential within a range bounded by any of these values, e.g., 25-45 volts.

In the disclosed methods, cells such as myotubule cells may be subjected to EPS conditions having a suitable frequency. Suitable frequencies may include, but are not limited to, at least about 0.5, 1, 2, 3, 4, 5, 6, 7, 8, 9, or 10 Hertz, or frequency within a range bounded by any of these values, e.g., 0.5-5 Hertz.

In some embodiments, the EPS conditions comprise an electrical potential of between about 15 V to about 50 V. In other embodiments, the period of time for exposing the myotubules to EPS conditions is from about 6 hours to about 24 hours, for example, from about 9 hours to about 12 hours. In other embodiments, the period of time for exposing the myotubules to EPS conditions is less than one hour, less than two hours, less than three hours, less than five hours, less than six hours, less than seven hours, less than eight hours, less than nine hours, less than ten hours less than eleven hours, less than twelve hours, less than fifteen hours, less than twenty hours, less than twenty-four hours, less than thirty-six hours, or less than forty-eight hours. In one preferred embodiment, the period of time for exposing the myotubules to EPS conditions is about nine hours.

The EPS conditions can be generated by any method and/or device known in the art to deliver electrical stimulation to cultivated cells in vitro. Non-limiting examples of commercially available devices useful for generating the EPS conditions are a C-Pace Cell Culture FP Stimulator (Ion Optix, Westwood, Mass., USA) and a Grass S-48 stimulator (Grass Instruments, Quincy, Mass., USA).

The disclosed compositions may comprise stimulated media, a fraction thereof, and/or one or more myokines. In some embodiments, the stimulated muscle medium and/or myokines of the disclosed compositions comprise myostatin, metrnl, TNF-α, IL-6, IP-10/CXCL10/CRG2, RANTES/CCL5, GM-CSF, I-309/CCL1/TCA-3, Serpin A8/Angiotensin II, or any combination thereof. In some embodiments, the stimulated muscle medium and/or myokines comprise no or substantially no cathepsin L (CTSL, CTSL1), pentraxin-3/TSG-14 (PTX3), adiponectin/Acrp30 (ADIPOQ), vascular endothelial growth factor (VEGF), angiopoietin-1 (ANGPT1), IGFBP-3, IGFBP-4, MIF, IGFBP-rp1/IGFBP-7, Serpin A12/Vaspin, TMP-1, KC/CXCL1, JE/CCL2/MCP-1, M-CSF, TNF-α or any combination thereof.

In some embodiments, centrifugal filters are ultrafiltration filters which can separate small particles and dissolved molecules from fluids based primarily on molecular size, are used to fractionate the muscle stimulated medium to isolate or concentrate for specific cytokines of interest. In some embodiments, the filter/membrane is regenerated cellulose, polyethersulfone (PES) or PVDF. In some embodiments, the ultrafiltration filters have a 3,000 nominal molecular weight limit (NMWL), a 5,000 NMWL, a 7,500 NMWL, a 10,000 NMW, a 15,000 NMWL, a 20,000 NMWL, a 30,000 NMWL, a 35,000 NMWL, a 40,000 NMWL, a 50,000 NMWL, a 60,000 NMWL, a 70,000 NMWL, 80,000 NMWL, a 90,000 NMWL, a 100,000 NMWL, or greater NMWL.

In some aspects, provided herein are compositions comprising an amount of stimulated muscle medium and/or myokines isolated therefrom and a pharmaceutical excipient. In some embodiments, the amount of stimulated muscle medium and/or myokines is a therapeutically effective amount.

The composition can comprise a pharmaceutically acceptable excipient, a pharmaceutically acceptable salt, diluents, carriers, vehicles and such other inactive agents well known to the skilled artisan. Vehicles and excipients commonly employed in pharmaceutical preparations include, for example, talc, gum Arabic, lactose, starch, magnesium stearate, cocoa butter, aqueous or non-aqueous solvents, oils, paraffin derivatives, glycols, etc. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions may be prepared using conventional techniques that may include sterile isotonic saline, water, 1,3-butanediol, ethanol, 1,2-propylene glycol, polyglycols mixed with water, Ringer's solution, etc.

Compositions may include a preservative and/or a stabilizer. Non-limiting examples of preservatives include methyl-, ethyl-, propyl-parabens, sodium benzoate, benzoic acid, sorbic acid, potassium sorbate, propionic acid, benzalkonium chloride, benzyl alcohol, thimerosal, phenylmercurate salts, chlorhexidine, phenol, 3-cresol, quaternary ammonium compounds (QACs), chlorbutanol, 2-ethoxyethanol, and imidurea.

In some embodiments, the composition may include a cryoprotectant agent. Non-limiting examples of cryoprotectant agents include a glycol (e.g., ethylene glycol, propylene glycol, and glycerol), dimethyl sulfoxide (DMSO), formamide, sucrose, trehalose, dextrose, and any combinations thereof.

In general, the compositions provided herein can be formulated for administration to a subject by any of the accepted modes of administration. Various formulations and drug delivery systems are available in the art. See, e.g., Gennaro, A. R., ed. (1995) Remington's Pharmaceutical Sciences, 18th ed., Mack Publishing Co. In some embodiments, the composition is formulated for intravenous, intraperitoneal, or intratumoral delivery. In other embodiments, the composition is present in a skin patch.

The compositions described herein are useful in treating diseases or disorders, for example, cancer and metabolic diseases such as fatty liver disease (i.e., NAFLD), diabetes, obesity, heart disease, and osteoporosis. In some aspects provided herein are methods of treating or preventing a cancer in a patient in need thereof comprising administering to the patient an effective amount of a composition comprising stimulated muscle medium and/or myokines isolated therefrom.

Cancers or tumors that can be treated by the compositions and methods described herein include, but are not limited to: biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; intraepithelial neoplasms, including Bowen's disease and Paget's disease; liver cancer (hepatocarcinoma); lung cancer; lymphomas, including Hodgkin's disease and lymphocytic lymphoma; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer, including adenocarcinoma and Wilms tumor. In some preferred embodiments, the cancer is breast cancer, colorectal cancer, endometrial cancer, hepatocellular carcinoma, non-small cell lung cancer, ovarian cancer, or prostate cancer. In some embodiments, the cancer is a solid tumor. In some embodiments, the solid tumor is reduced in size.

An effective amount of such compositions can readily be determined by routine experimentation, as can the most effective and convenient route of administration, and the most appropriate formulation. An effective amount or a therapeutically effective amount or dose of a composition refers to the amount of the composition that results in amelioration of symptoms or a prolongation of survival in a subject. Toxicity and therapeutic efficacy of such compositions can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Compositions that exhibit high therapeutic indices are preferred.

In some embodiments, the composition is administered by direct injection or perfusion into the solid tumor. In other embodiments, the composition is administered intravenously, intraperitoneally, or intratumorally.

In some embodiments of the disclosed methods, a subject is administered a second therapeutic that is different than said stimulated muscle medium and/or myokines isolated therefrom. The therapeutic can be any useful agent and/or procedure for the treatment, remission or attenuation of a disease state, physiological condition, symptoms, or etiological factors, or for the evaluation or diagnosis thereof. A therapeutic agent may be a chemotherapeutic agent, for example, mitotic inhibitors, topoisomerase inhibitors, steroids, anti-tumor antibiotics, antimetabolites, alkylating agents, enzymes, proteasome inhibitors, immunotherapy, any combinations thereof and the like. Therapeutic procedures include radiation, surgery, and the like.

In some embodiments, the methods for treating and/or preventing disease or disorder in a subject in need thereof, the methods comprise administering to the subject a second therapeutic agent that is different from the stimulated muscle medium, an isolated fraction thereof, and/or myokines isolated therefrom. In some embodiments, the second therapeutic agent comprises a platinum-based therapeutic agent (e.g., carboplatin, cisplatin, oxaliplatin, and triplatin). In some embodiments, the second therapeutic is selected from the group consisting of abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, paclitaxel, pazopanib, pemetrexed, picoplatin, romidepsin, satraplatin, sorafenib, vemurafenib, sunitinib, teniposide, triplatin, vinblastine, vinorelbine, vincristine, and cyclophosphamide. In some embodiments, a sub-therapeutic dose of the second therapeutic is administered. In some embodiments, the stimulated muscle medium and/or myokines and the second therapeutic are delivered substantially simultaneously, concurrently or sequentially.

In some embodiments, a sub-therapeutic dose of the second therapeutic is administered to the subject. "Sub-therapeutic" means an amount less than that which normally would produce an anxiolytic effect when given to a subject. In some embodiments, the sub-therapeutic amount is one quarter to one half the normal daily dosage. In some embodiments, the stimulated muscle medium and/or myokines and the second therapeutic are delivered substantially simultaneously, concurrently or sequentially.

Fatty liver disease (FLD, also known as hepatosteatosis) is a prevalent liver condition that occurs when lipids accumulate in liver cells, unrelated to alcohol use, but linked to obesity, diabetes and dyslipidemia. The lipid accumulation causes cellular injury and sensitizes the liver to further injuries. The accumulated lipids may also impair hepatic microvascular circulation. In other aspects provided herein are methods of treating and/or preventing fatty liver in a patient in need thereof comprising administering to the patient an effective amount of stimulated muscle medium and/or myokines.

The disclosed methods may be utilized for generating, preparing, and/or isolating myokines from a culture media. In some embodiments, the disclosed methods may include subjecting myotubules in a culture medium to electrical pulse stimulation (EPS) conditions. The myotubules may be subjected to EPS conditions to stimulate the myotubules to secrete myokines into culture media and prepare so-called "stimulated media" which may simulate muscle medium. The stimulated media may be isolated from the myotubules. The stimulated media may be further fractionated and/or treated to isolate fractions comprising, consisting essentially of, or consisting of, one or more specific myokines. The isolated fractions comprising one or myokines may be formulated as pharmaceutical compositions comprising the one or more myokines and a pharmaceutical carrier, excipient, or diluent for treating diseases and disorders including cell proliferative diseases or disorders and metabolic diseases and disorders. Also disclosed are methods of treating and/or preventing a cancer or a metabolic disease in a subject in need thereof comprising administering to the subject an effective amount of a composition comprising stimulated muscle medium and/or myokines isolated therefrom.

The disclosed composition may comprise additional components. In some embodiments, the compositions comprise a preservative, a cryopreservative, a carrier protein, or combinations thereof.

The disclosed compositions may be formulated for delivery to a subject in need thereof. In some embodiments, the composition is formulated for intravenous, intraperitoneal, or intratumoral delivery. In other embodiments, the composition is present in a skin patch.

The disclosed methods may be utilized to reduce the size of a solid tumor in a subject in need thereof. In some embodiments, the disclosed compositions are administered by direct injection or perfusion into the solid tumor. In other embodiments, the disclosed compositions are administered intravenously, intraperitoneally, intratumorally, subcutaneously, or orally.

The disclosed methods may be utilized to treat and/or prevent metabolic diseases or disorders in a subject in need thereof. In some embodiments, the subject has a disease or disorders selected from a fatty liver disease, dyslipidemia, metabolic syndrome, a cardiovascular disease, obesity, a leptin disorder, or any combination thereof. In some embodiments, the fatty liver disease is hepatic steatosis, non-alcoholic steatohepatitis, non-alcoholic fatty liver disease (NAFLD), elevated liver cholesterol level, elevated liver triglyceride level, elevated liver fatty acid level, elevated liver LDL-cholesterol level, elevated liver VLDL cholesterol level, or elevated liver non-HDL cholesterol level, or any combination thereof.

ILLUSTRATIVE EMBODIMENTS

The following embodiments are illustrative and should not be interpreted to limit the scope of the claimed subject matter.

Embodiment 1

An isolated fraction of myokines comprising an effective amount of one or more myokines for treating and/or preventing cell proliferative diseases ordisorders and/or metabolic diseases or disorders, wherein (i) the one or more myokines have a molecular weight greater than about 10 kDa; and/or (ii) the one or more myokines comprise myostatin, metrnl, or both of myostain and metrnl.

Embodiment 2

The isolated fraction of myokines of embodiment 1, wherein the isolated fraction of myokines comprises an effective amount of one or more myokines for treating colorectal cancer.

Embodiment 3

The isolated fraction of any of the foregoing embodiments, wherein the isolated fraction of myokines comprises an effective amount of one or more myokines for treating a cancer whose growth is associated with chromatin density.

Embodiment 4

The isolated fraction of myokines of any of the foregoing embodiments, wherein the isolated fraction of myokines comprises an effective amount of one or more myokines for treating a cancer whose growth is associated with epidermal growth factor receptor (EGRF) activity.

Embodiment 5

The isolated fraction of myokines of any of the foregoing embodiments, wherein the isolated fraction of myokines comprises an effective amount of one or more myokines for inhibiting epidermal growth factor receptor (EGRF) activity.

Embodiment 6

A pharmaceutical composition comprising the isolated fraction of myokines of any of the foregoing embodiments and a suitable pharmaceutical carrier.

Embodiment 7

A kit for treating and/or preventing cell proliferative diseases and disorders, the kit comprising a combination of components comprising: (i) the isolated fraction of myokines of any of the foregoing embodiments; and a chemotherapeutic drug for treating and/or preventing the cell proliferative disease or disorder.

Embodiment 8

The kit of embodiment 7, wherein the kit comprises myostatin and a platinum-based chemotherapeutic agent.

Embodiment 9

The kit of embodiment 7 or 8, wherein the kit comprises myostatin and oxaliplatin.

Embodiment 10

The kit of any of embodiments 7-9, wherein the kit comprises metrnl and a platinum-based chemotherapeutic agent.

Embodiment 11

The kit of any of embodiments 7-10, wherein the kit comprises metrnl and oxaliplatin.

Embodiment 12

A method for treating and/or preventing a cell proliferative disease or disorder in a subject in need thereof, the method comprising administering to the subject the isolated fraction of myokines of any of the foregoing embodiments or a pharmaceutical formulation thereof.

Embodiment 13

The method of embodiment 12, wherein the cell proliferative disease or disorder is colorectal cancer.

Embodiment 14

A method for treating and/or preventing a cell proliferative disease or disorder in a subject in any of the kits of embodiments 7-11, or a pharmaceutical formulation thereof, wherein the components are administered simultaneously, or one compound is administered before or after the other component.

Embodiment 15

A method for treating and/or preventing a cell proliferative disease or disorder in a subject in need thereof, the method comprising administering to the subject the subject the isolated fraction of myokines of embodiment 1 or a pharmaceutical formulation thereof, and administering to the subject a chemotherapeutic drug for treating and/or preventing the cell proliferative disease or disorder.

Embodiment 16

The method of embodiment 15, wherein the cell proliferative disease or disorder is colorectal cancer.

Embodiment 17

The method of embodiment 15 or 16, wherein the isolated fraction of myokines comprises myostatin.

Embodiment 18

The method of any of embodiments 15-17, wherein the isolated fraction of myokines comprises metrnl.

Embodiment 19

The method of any of embodiments 15-18, wherein the chemotherapeutic drug is a platinum-based drug.

Embodiment 20

A method for preparing an isolated myokine fraction, the method comprising (a) treating myotubules in a media culture with a electrostimulation wherein one or more of the following conditions are met (i) the myotubules are treated with electrostimulation for at least about 4 hours; (ii) the myotubules are treated with a voltage of at least about 20 V; and the myotubules are treated with a frequency of at least about 2 Hz; (b) isolating a myokine fraction released from the electrostimulated myotubules.

21

An isolated fraction of myokines for use in treating and/or preventing cell proliferative diseases and disorders (e.g., cancer) and/or metabolic diseases and disorders (e.g., diabetes), preferably wherein the isolated fraction of myokines comprises, consists essentially of, and/or consists of myostatin.

22

The isolated fraction of embodiment 21, wherein the isolated fraction modulates (e.g., inhibits) the activity of epidermal growth factor receptor (EGFR) activity.

23

A method for treating and/or preventing a cell proliferative disease and disorder (e.g., cancer) in a subject in need thereof, the method comprising administering to the subject a myokine or combination of myokines (e.g., a myokine and/or combination of combination of myokines released from myotubules such as stimulated myotubules).

24

A method for treating and/or preventing a metabolic disease and disorder (e.g., diabetes) in a subject in need thereof, the method comprising administering to the subject a myokine or combination of myokines (e.g., a myokine and/or combination of combination of myokines released from myotubules such as stimulated myotubules).

25

A method comprising isolating and/or concentrating a myokine and/or a combination of myokines released from myotubules (optionally wherein the myotubules are stimulating, for example, by electrostimulation), and optionally, further selecting a myokine and/or combination of combination of myokines released from myotubules by administering the myokine and/or combination of myokines released from myotubules in a cancer cell model and/or a metabolic disease cell model and detecting modulation of cell proliferation or death and/or metabolism by the myokine and/or combination of myokines released from myotubules in the cancer cell model and/or the metabolic disease cell model.

EXAMPLE

The following examples are illustrative and should not be interpreted to limit the scope of the claimed subject matter.

Example 1

Technical Field

The technical field relates to the identification and use of myokines for identification and use of myokines for treating and/or preventing cell proliferative and metabolic diseases and disorders.

Abstract

Exercise has well established salutary effects on both cancer risk/therapy and metabolic diseases. While the mechanism of action may be multifactorial, recent data has suggested that small hormone-like molecules (i.e., cytokines) secreted by the contracting muscle and termed "myokines" may be responsible.

Given the large number of potential myokines, we have developed and modified a system for generating myokines in cell culture which enables precise identification of the myokines, either alone or in combination that would have the greatest effect for treating diseases and disorders such as cell proliferative diseases and disorders and metabolic diseases and disorders.

Here, we note for the first time that our system can identify myokines that target specific receptors on the cell surface such as epidermal growth factor (EGFR). Targeting EGFR has been previously explored as an anti-cancer therapy but current drugs either have only modest efficacy or exhibit toxicity. We also note for the first time that our system can identify myokines that modulate chromatin structure and hence regulate gene expression. Our system has the potential to identify a new set of therapeutic agents to treat and/or prevent diseases and disorders such as cell proliferative diseases and disorders and metabolic diseases and disorders.

Applications

The applications of the disclosed technology include, but are not limited to: (i) decreasing the risk of cancer development; (ii) increasing the efficacy of chemotherapy agents by targeting receptor tyrosine kinases and chromatin structure; and (iii) impacting metabolic diseases such as diabetes, non-alcoholic fatty liver disease (NAFLD) and heart disease.

Advantages

The advantages of the disclosed technology include, but are not limited to: (i) providing a platform for drug discovery focusing on diseases that appear to be exercise responsive; (ii) enabling isolation of particular myokines or combinations of myokines (i.e., myokine cocktails) to increase efficacy of receptor kinase inhibition through direct binding; and (iii) giving that myokines are made by the body, toxicity is predicted to be less than current approaches for treating cell proliferative diseases and disorders that utilize monoclonal antibodies or small molecule inhibitors.

Brief Summary of the Disclosed Technology

There is compelling epidemiological evidence of the salutary effects of physical activity (exercise) on various aspects of health. For instance, exercise reduces the incidence of mortality from cancer. Exercise is one of the major protectors against metabolic diseases such as diabetes, fatty liver (NAFLD) and heart disease.

The mechanism of action is undoubtedly pleotropic but several lines of evidence suggest that cytokines (i.e., small molecules that act as hormones in that they have a specific effect on target tissues that express specific cellular receptors) released by contracting muscles may be important. These cytokines released by muscles are termed "myokines" and there are ~3000 identified to date. Candidate approaches have yielded several myokines that have efficacy in malignant or metabolic diseases. However, these myokines do not recapitulate all of the effect and there are probably multiple myokines and also myokine-myokine interactions important for treating malignant and metabolic diseases. This argues for the development of a platform approach.

We have adapted a cell culture system to serve as a platform for myokine and hence drug discovery. Specifically, we utilize C2C12 (myoblast cell line) and differentiate them into myotubules. We then subject these myotubules to electric stimulation (IonOptic Cell Pace System) and isolate/concentrate molecules released from the myotubules by molecular weight fractionation. We administer these isolated/concentrated myokine fractions in cell line models of cancer or metabolic diseases and demonstrate efficacy through changes in various well-established molecular pathways.

We have validated this model by showing the efficacy of these myokines alone and/or through augmentation of chemotherapy in various cancer cell lines including colon, lung, breast, liver, prostate and pancreatic cancer. With regards to metabolic diseases, we have shown suppression of fat accumulation in liver cells.

With regards to molecular targets, we hypothesize that myokines released by exercise might target cell surface receptors that act as proto-oncogenes. One promising target in cancer is epidermal growth factor receptor (EGFR). EGFR is an oncogene in many cancer types and several multi-billion dollar drugs (e.g., monoclonal antibodies cetuximab and panitumumab along with small molecule inhibitors such as erlotinib and gefitinib) have been developed. Specifically, in cell culture assays we show that specific myokine fractions isolated/concentrated in our systems suppress EGFR activity. Importantly, we show that these myokines directly physically interact with and inhibit EGFR, suggesting a novel mechanism of action. The market opportunities are large, even for this target alone, and there are numerous other potential targets.

To further refine our target selection, we analyze change in overall transcriptional (gene expression) ability through a novel nano-architectural technology developed by the Backman laboratory called live cell partial wave spectroscopic (PWS) microscopy. Using PWS we are able to interrogate alterations in chromatin structure at scales from ~kbp to a few Mbp, which has been implicated in the regulation of the phenotypic plasticity of cells (e.g. cancer cells) including transcriptional malleability and intercellular heterogeneity. In turn, phenotypic plasticity is a critical factor that allows cancer cells to adapt to stressors, such as anti-cancer therapies.

Thus, we believe we have a platform for drug discovery that may serve to identify the optimal cocktail of myokines for therapeutic response to cancer and metabolic diseases. The platform can be used to identify new druggable targets leading to an opportunity of developing small molecule inhibitors through rational drug design.

Our preliminary studies used the human colorectal cancer cell line HT29. We generated our myokine fractions from C2C12 after differentiating them into myotubules and contracting by electric stimulation using the IonOptic system. The mykokines were fractionated and concentrated using the 10 kDa Amicon collection tubes. (See FIG. 1). As indicated, contractile cells are exposed to a variable current that makes them contract. Contracting cells synthesize about 3000 myokines.

Figure 2:
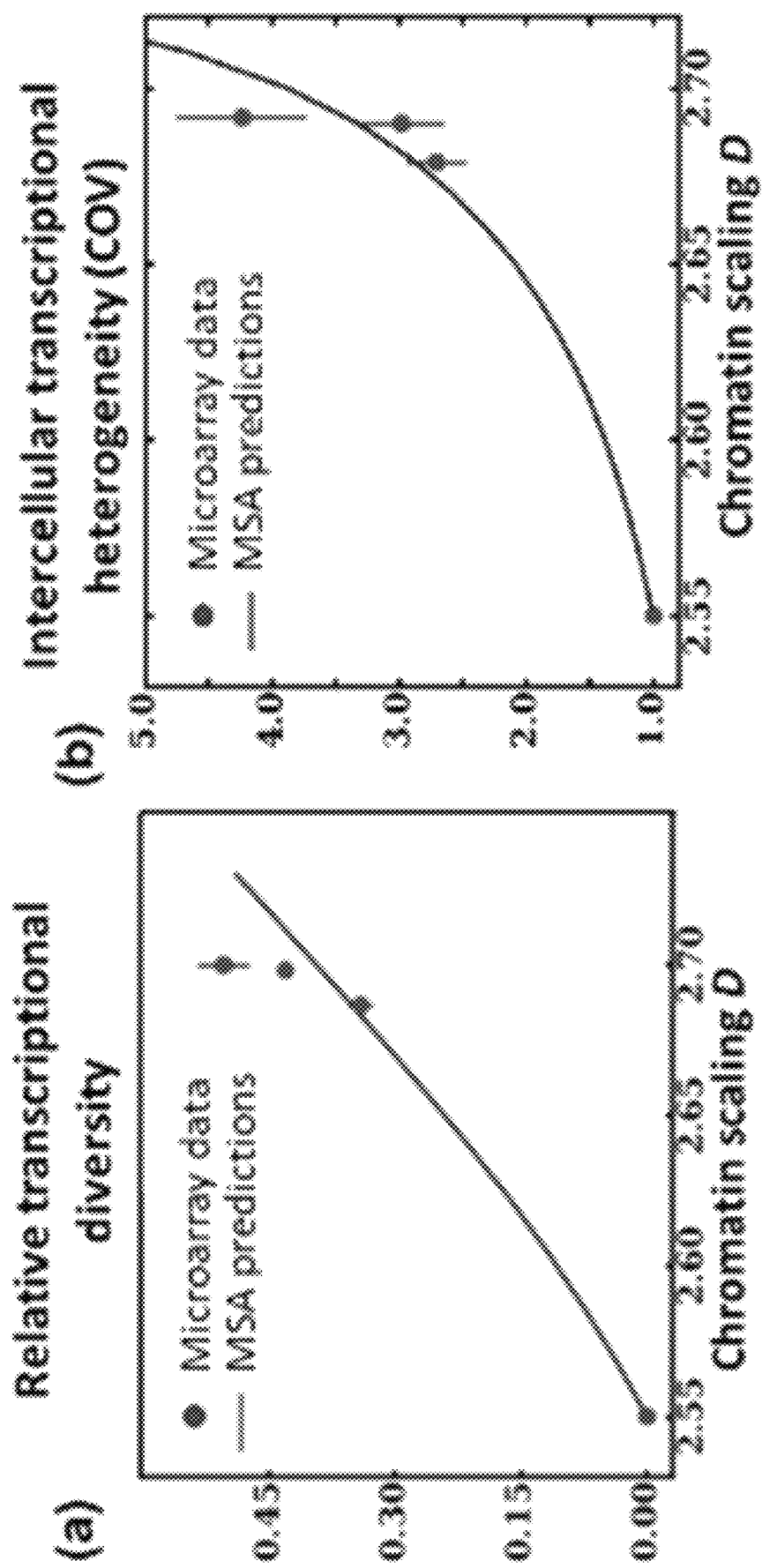
FIG. 2. Four aspects of transcriptional heterogeneity regulation by chromatin D: (a) diversity (the relative dynamic range of expression; HT29 cells, 2445 genes), (b) intercellular heterogeneity, (c) intranetwork heterogeneity, and (d) amplification of changes in expression (ratio of changes in the expression rate of 800 significant genes induced by paclitaxel in A2780 ovarian cancer cells for high- vs. low-D cells). Predictions of a computational transcriptomics (multiscale analysis, MSA) model are shown as blue curves. (e) Chemotherapy leads to the survival of cancer cells with high D (middle-top panel; live cell PWS images of D; arrows: nuclei) and transcriptional (right-top) heterogeneity, while CPT agents (digoxin) decrease both (bottom). Left panels: MSA simulations of chromatin packing show a CPT-induced transition from a network to polymer-like packing. (f) Cells surviving chemotherapy treatment (paclitaxel (PAC); 48 h, A2780) have a larger global transcriptional space (single cell sequencing) while CPT (celecoxib) reduces it. (g) PWS images of HCT116 colon cancer cells after treatment with chemotherapy (oxaliplatin), CPT (celecoxib), and their combination. The addition of a CPT leads to >98% cancer cell death. (h) CPT significantly increases the efficacy of chemotherapeutic agents independent of the mechanism of cytotoxicity. Mild CPTs (<5% D↓) are less effective than moderate CPTs (>5% D↓). Key: docetaxel (D), paclitaxel (P), oxaliplatin (0), digoxin (D), celecoxib (C), VPA (V), aspirin (A). (i) Synergistic lethality of CPT+chemotherapy relative to chemotherapy is proportional to the efficacy of CPTs to reduce D. (j) Cancer stem cells (ALDH(+) OvCar5) have a higher D compared to their non-stem (ALDH−,CD133−) counterparts. (k) Validation of CPT (9-ING-41) in vivo on the pancreatic ductal carcinoma PDX model. Animals were treated i.p. 3× a week with a chemotherapy drug gemcitabine (10 mg/kg) and/or 9-ING-41 (40 mg/kg). The CPT+gemcitabine co-treatment produced shrinkage in tumor volume <4% of the initial size.
Figure 2:
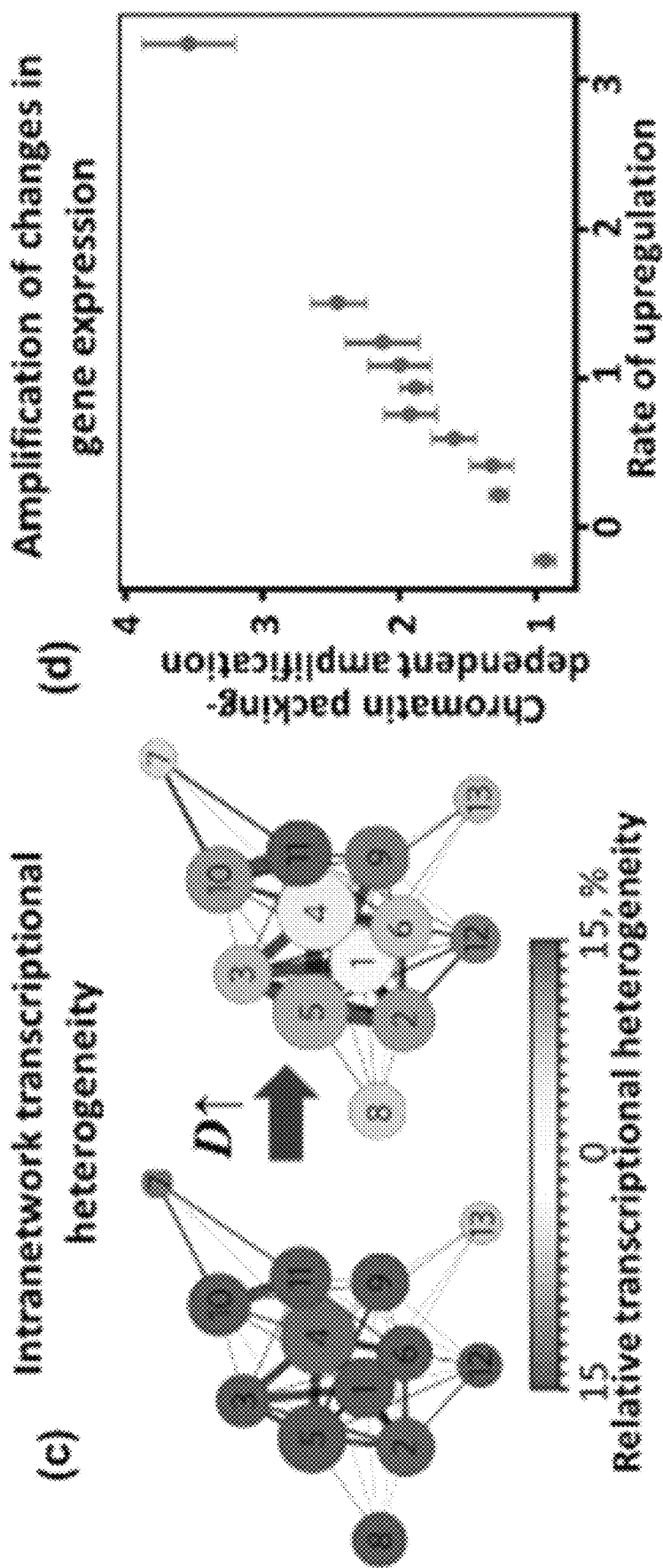
Figure 2:
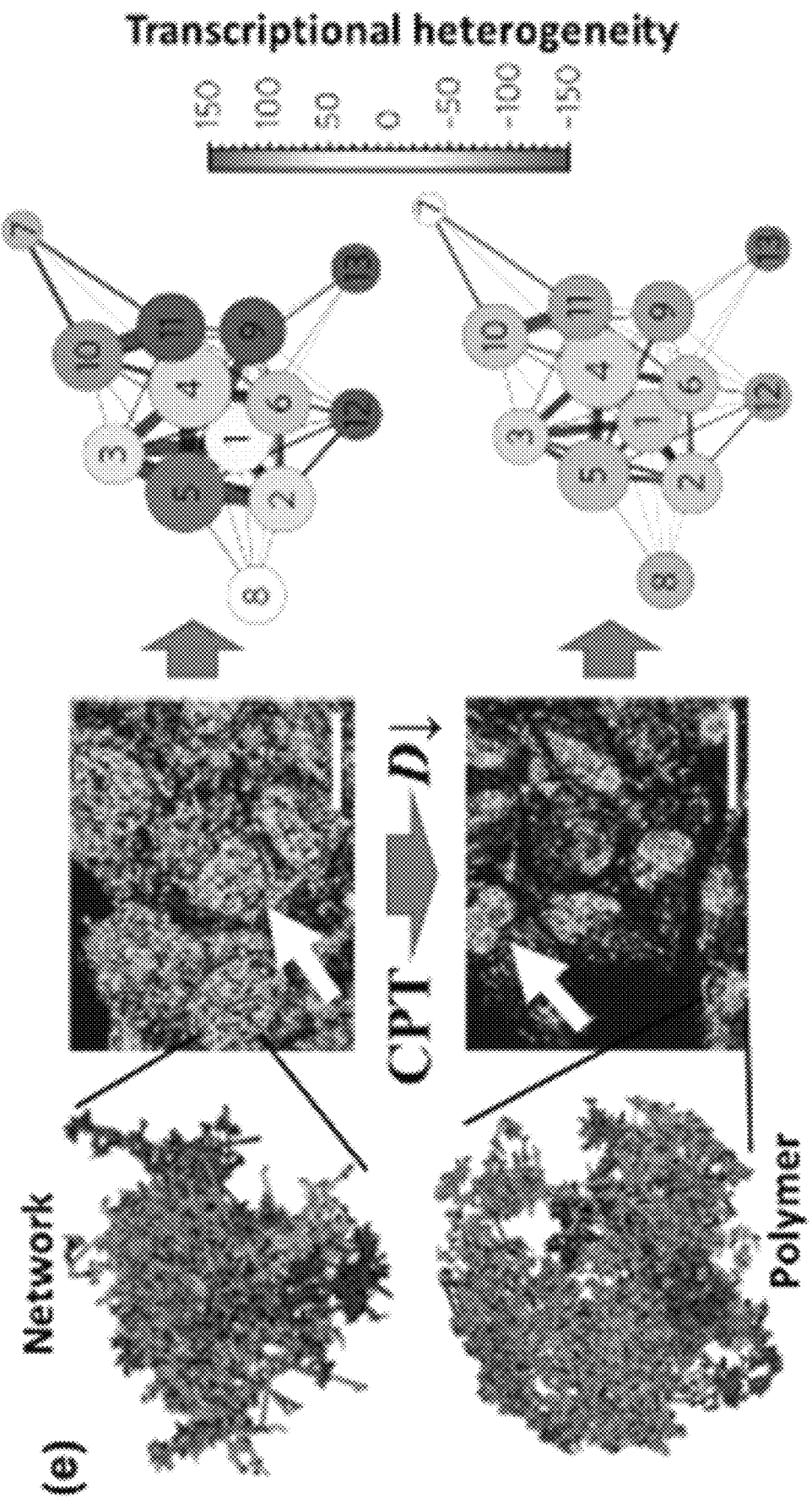
Figure 2:
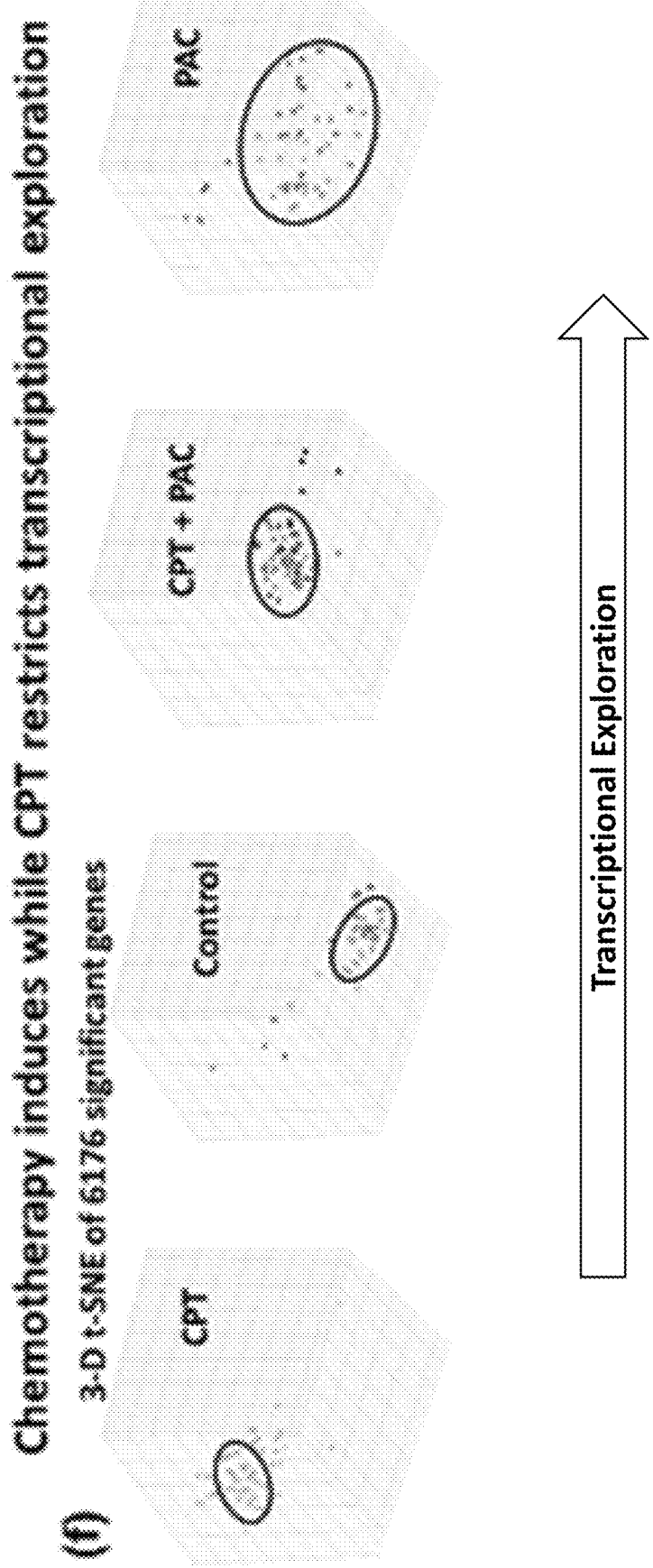
Figure 2:
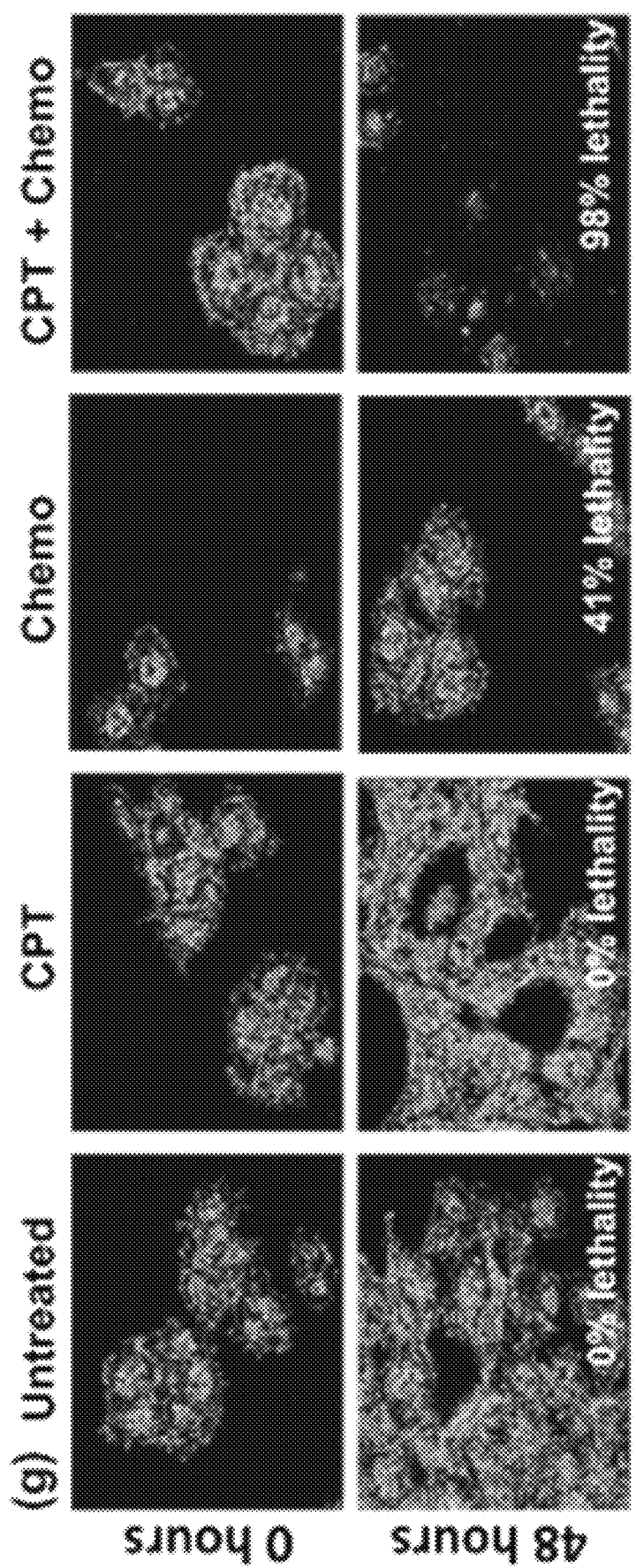
Figure 2:
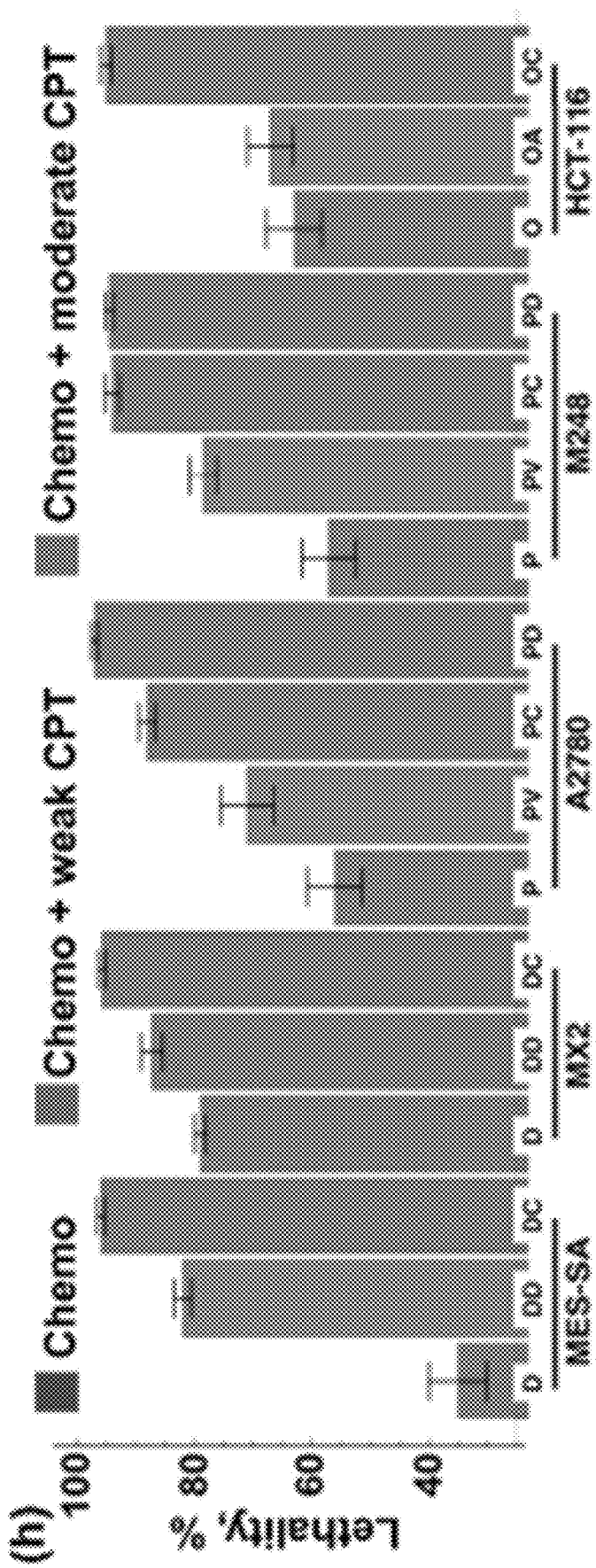
Figure 2:
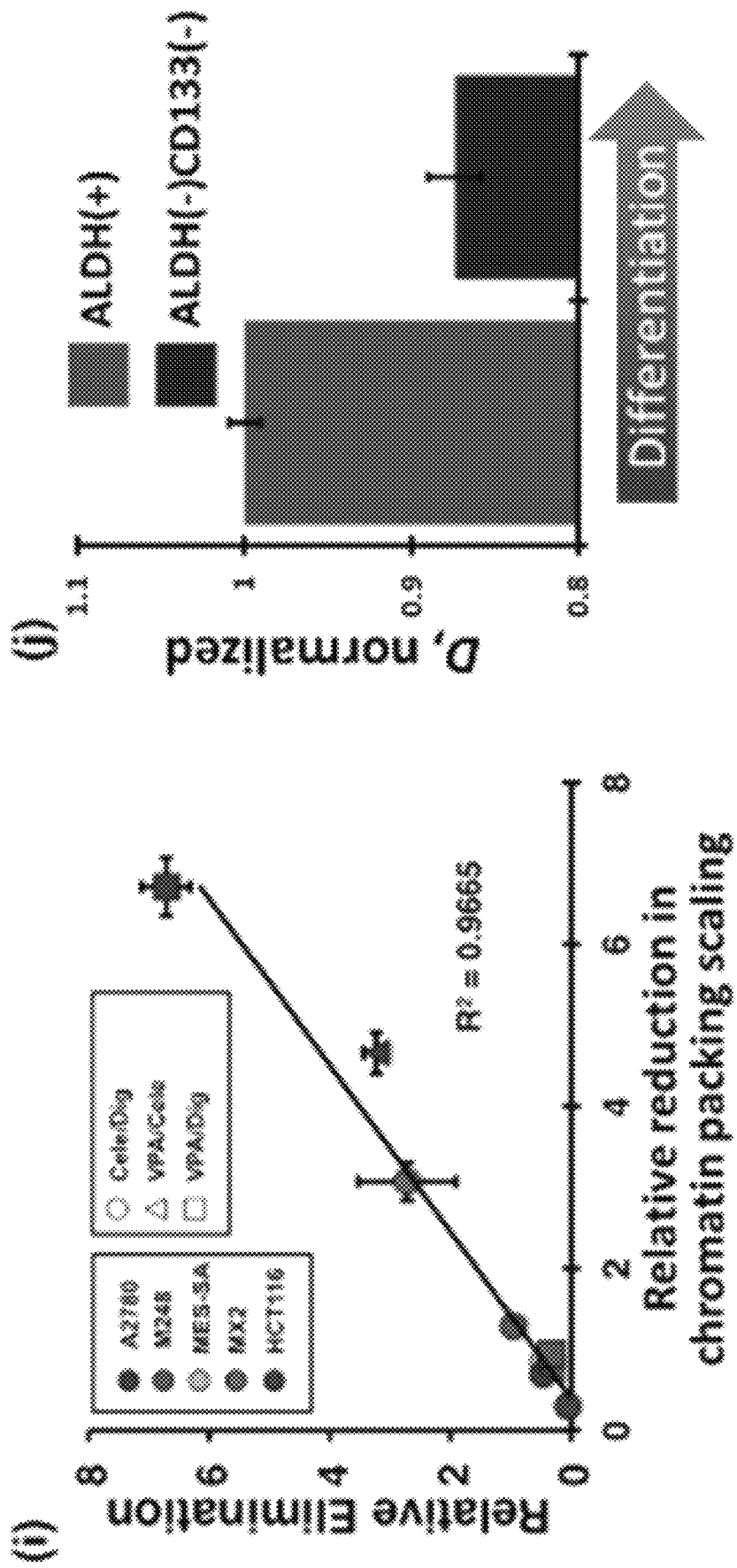
Figure 2:
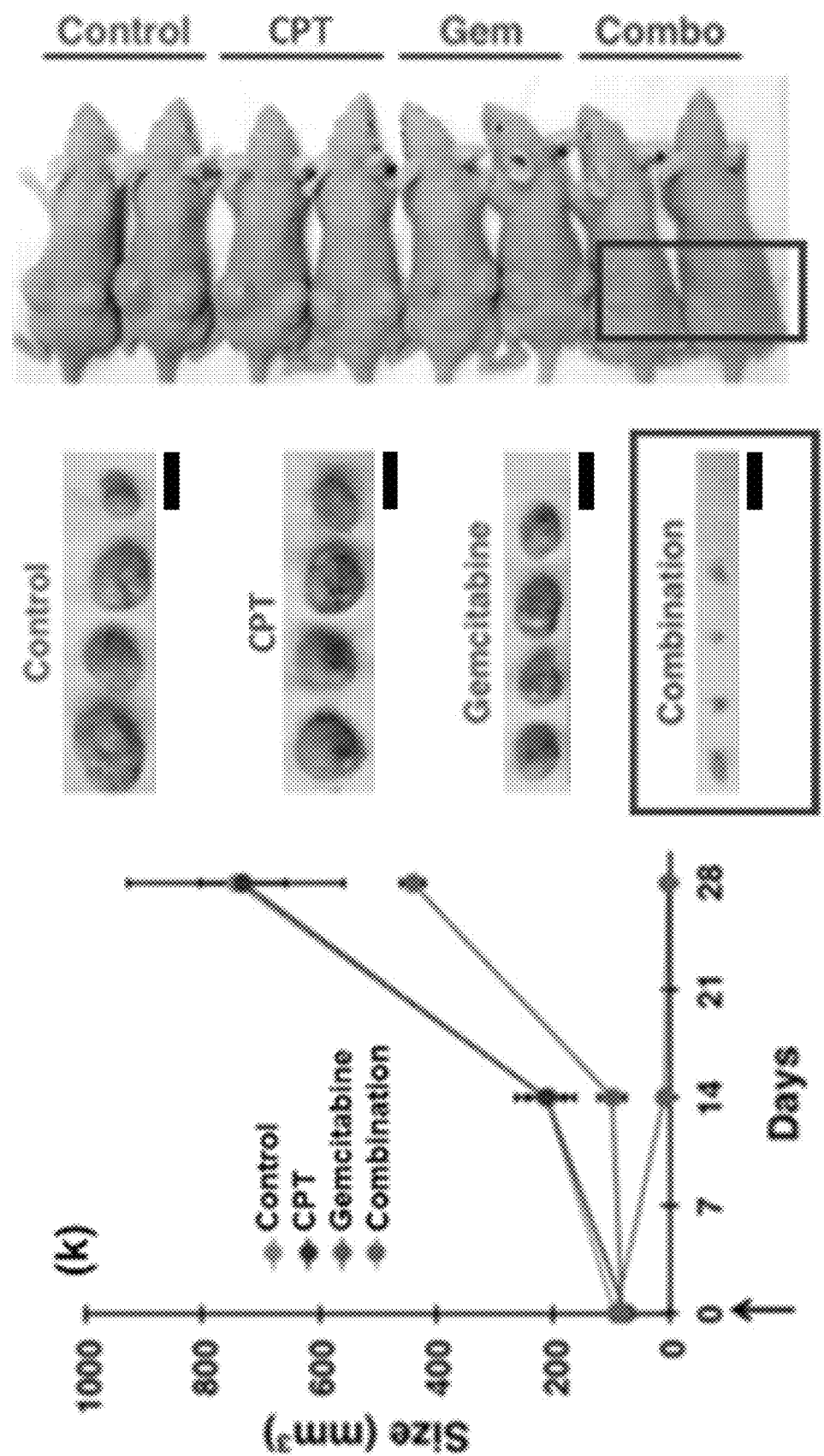
Figure 3:
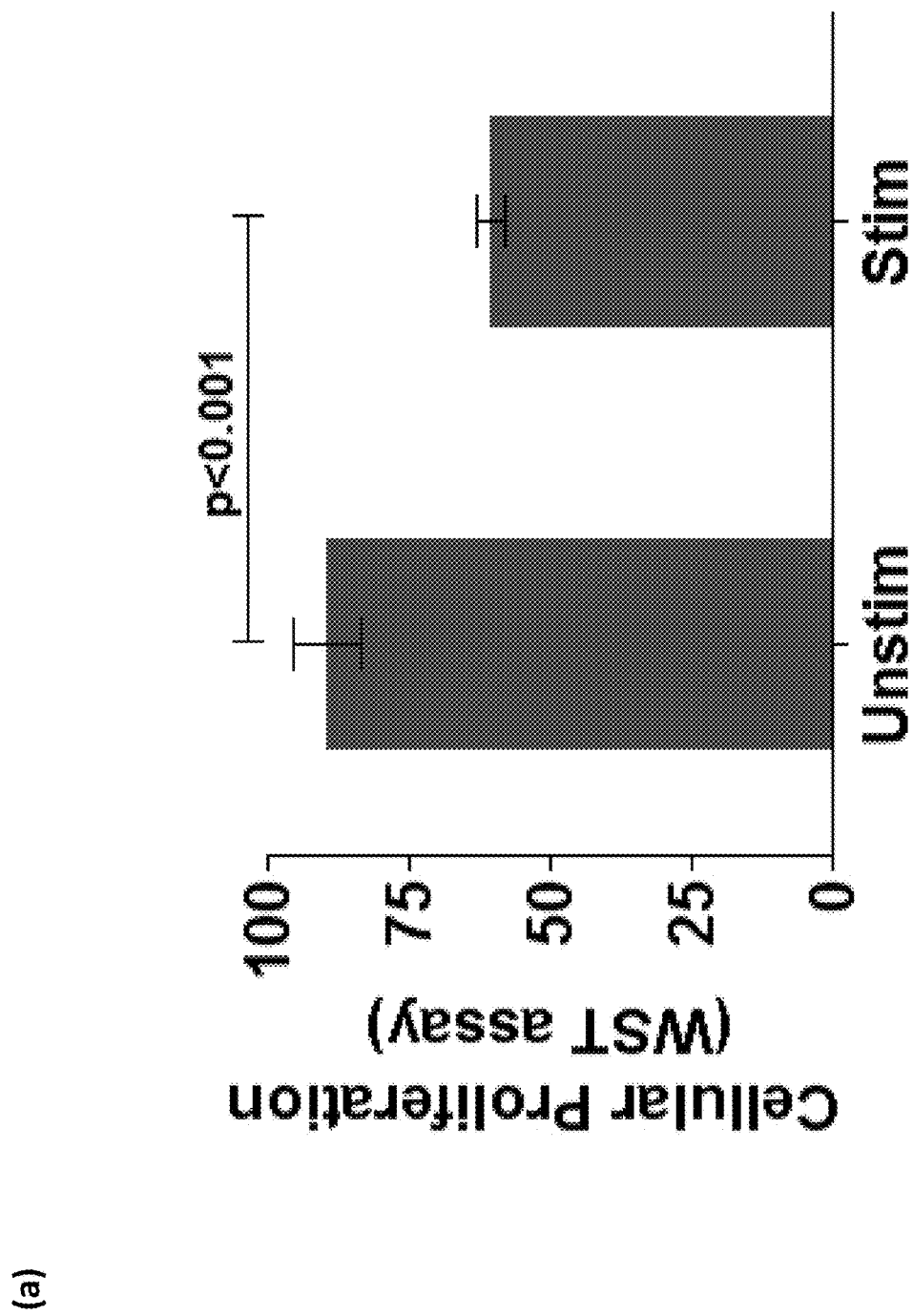
FIG. 3. Effect of exercise induced myokines on cancer cells. (a) WST-1 assay for the measurement of cellular proliferation of HT-29 cells treated with exercise stimulated media for 48 hrs. (b) Western blott analysis of cellular proliferation markers using cell lysates of HT29 and HCT116 cells treated with exercise stimulated media for 48 hrs. (c) LC-PWS analysis of HCT116 cells treated with exercise stimulated media for 2 hrs and 24 hrs.
Figure 3:
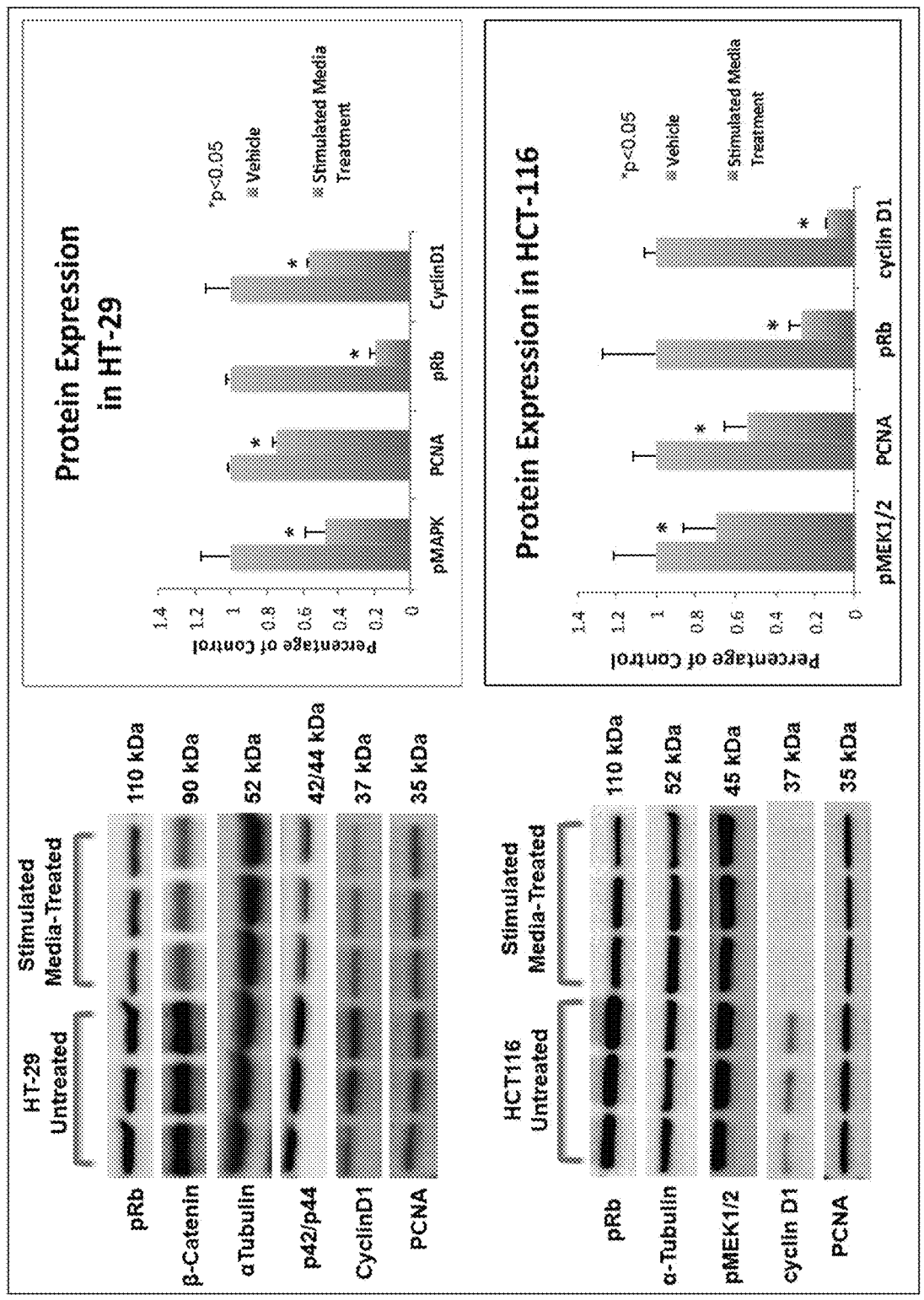
Figure 3:
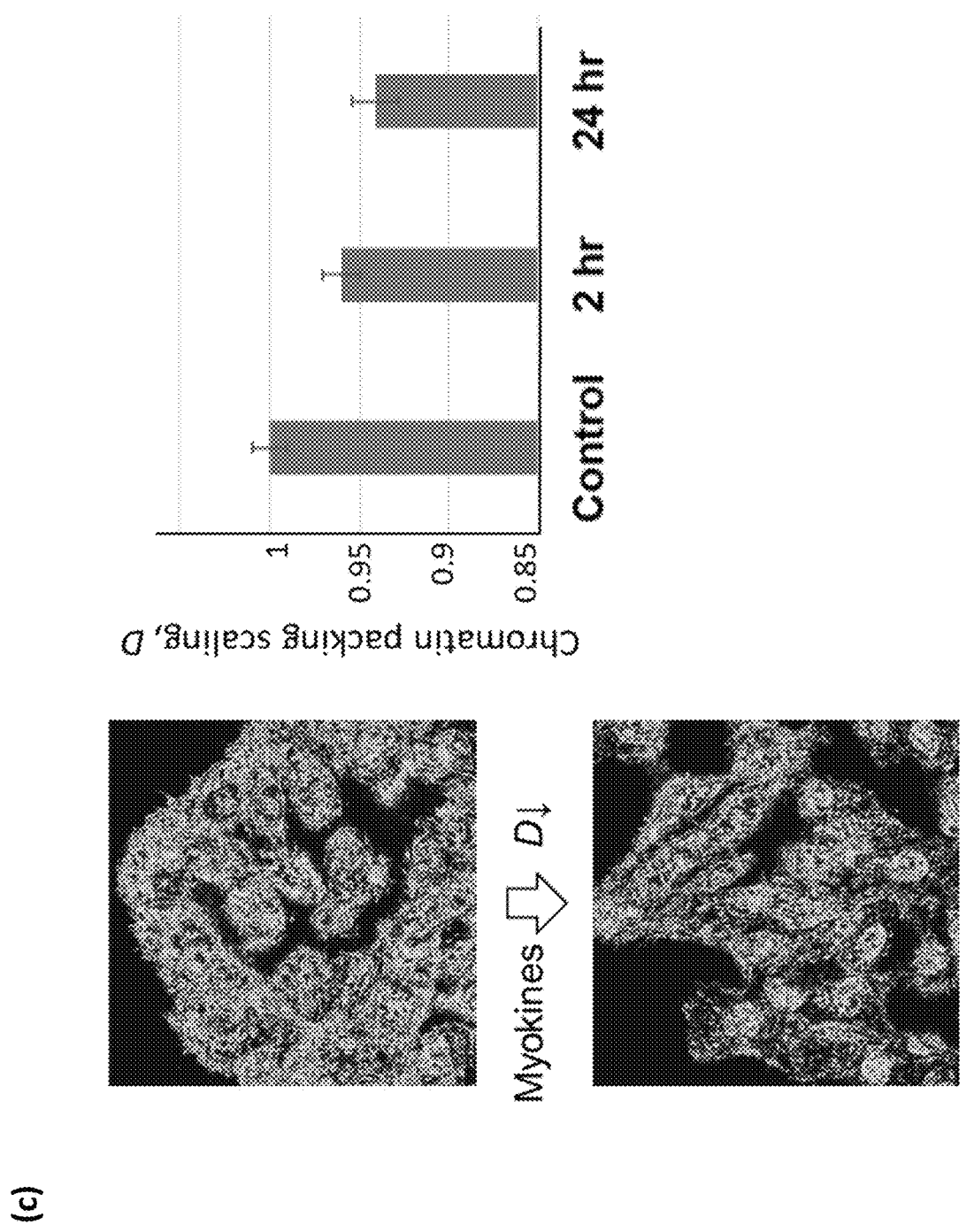
Figure 4:
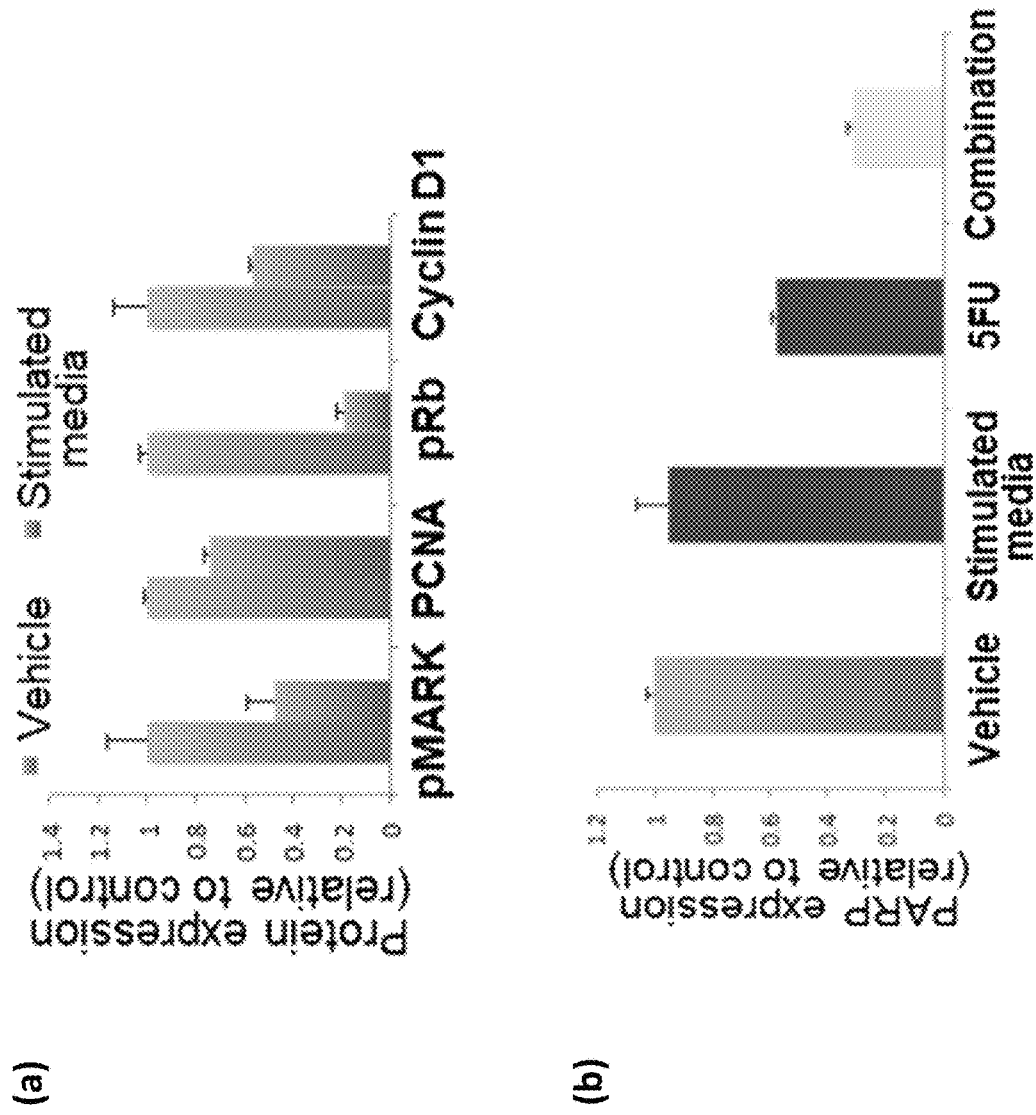
FIG. 4. The myokinome (stimulated media) inhibits protein expression (a) and PARP expression (b).

We have also demonstrated that myokines are able to modulate high order chromatin structure with potential significant implications for addressing diseases and processes where global genomic modulation plays a role such as cancer, tissue regeneration, cell resilience in response to injury, and stem cell technologies. The 3D organization of the genome is a subject of rapidly-evolving research. The emerging picture is that the genome is a disordered polymer packed into a variety of domains. The resulting chromatin packing density ($\varphi$) is highly non-uniform throughout the genome. Locally (~30 nm), $\varphi$ has a non-monotonic effect on gene expression, enhancing and suppressing it for $\varphi$ below and above 35%, respectively, due to the competing effects of molecular crowding, increased binding of transcriptional complexes and suppressed diffusion. Further effects are driven by the scaling of chromatin packing density (D) in the kbp—Mbp range (~20-350 nm). As in other polymeric systems, D links the physical and genomic sizes of a chromatin region. In turn, D affects the heterogeneity of chromatin packing and its accessibility, with the net effect of D↑ being a greater dynamic range of transcriptional states (transcriptional divergence), intercellular transcriptional heterogeneity, gene network heterogeneity, and the amplification of the rate of change in up/downregulation of gene expression, as shown below. D↑ lowers the barrier for changes in cellular functional activity. Cancer cells must keep developing new traits throughout tumor progression. Altered chromatin packing enables this process. Our data shows that stimulated myokinome decreases D with efficacy dependent on the stimulation protocol ($p<0.001$), has an antiproliferative effect, and synergizes with CRC chemotherapy (5-FU, HT29 cells). (See FIG. 2 and FIG. 3). We also observed that the myokinome inhibits protein expression of tumorigenic proteins. (See FIG. 4).

Figure 5:
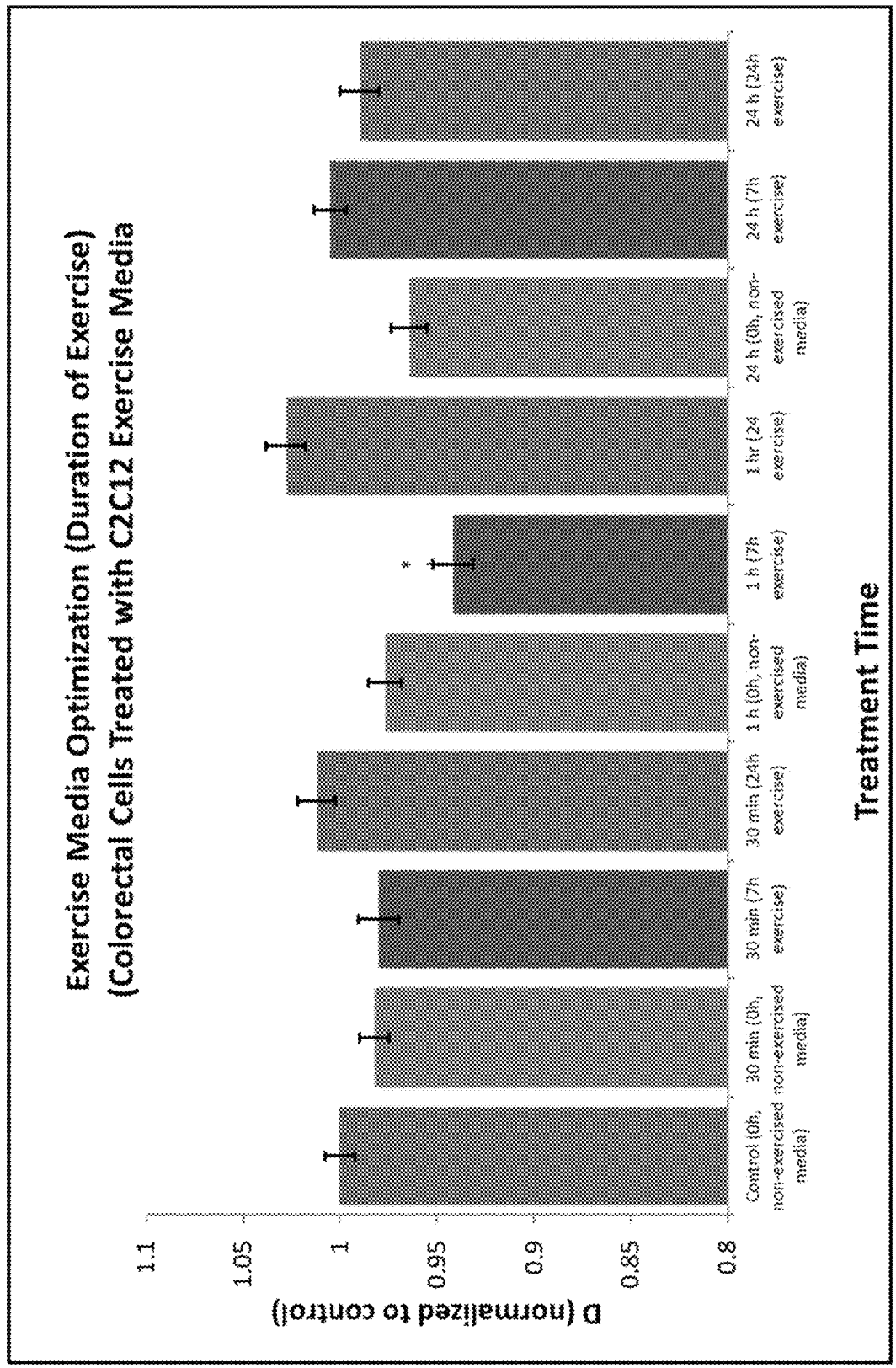
FIG. 5. Optimizing conditions for producing stimulated media which modulates chromatin density (D). (a) chromatin density (D) in colorectal cancer cells versus treatment time with stimulated media produced from myotubules subjected to variations in duration of exercise (i.e., duration of time that myotubules are stimulated with current). (b) chromatin density (D) of colorectal cancer cells versus treatment time with stimulated media produced from myotubules subjected to variation in intensity of voltage. (c) chromatin density (D) of colorectal cancer cells versus treatment time with stimulated media produced from myotubules subjected to variation in frequency (Hz). (d) chromatin density in colorectal cancer cells treated with myokine fraction having molecular weight greater than 10 kDa.
Figure 5:
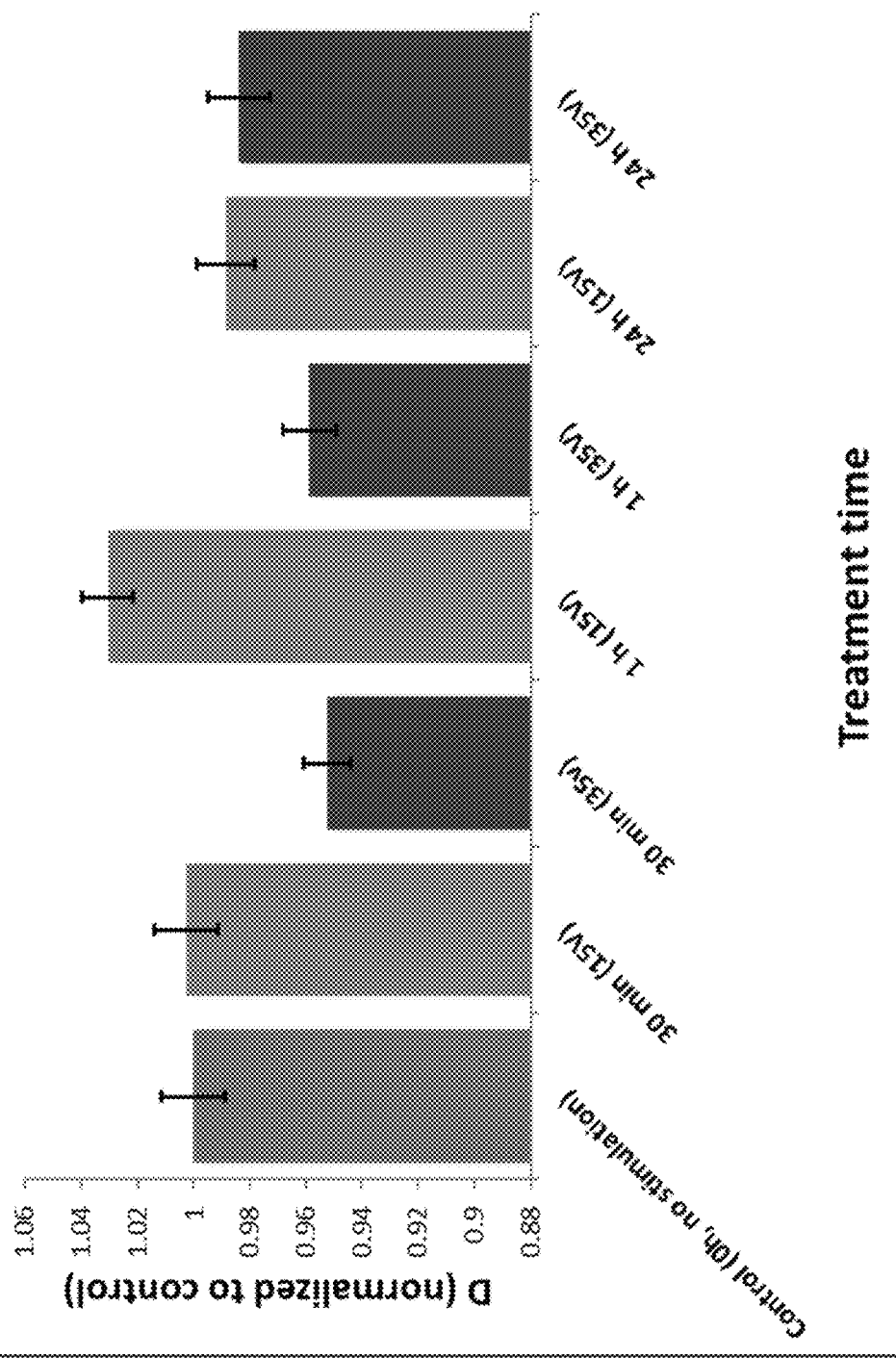
Figure 5:
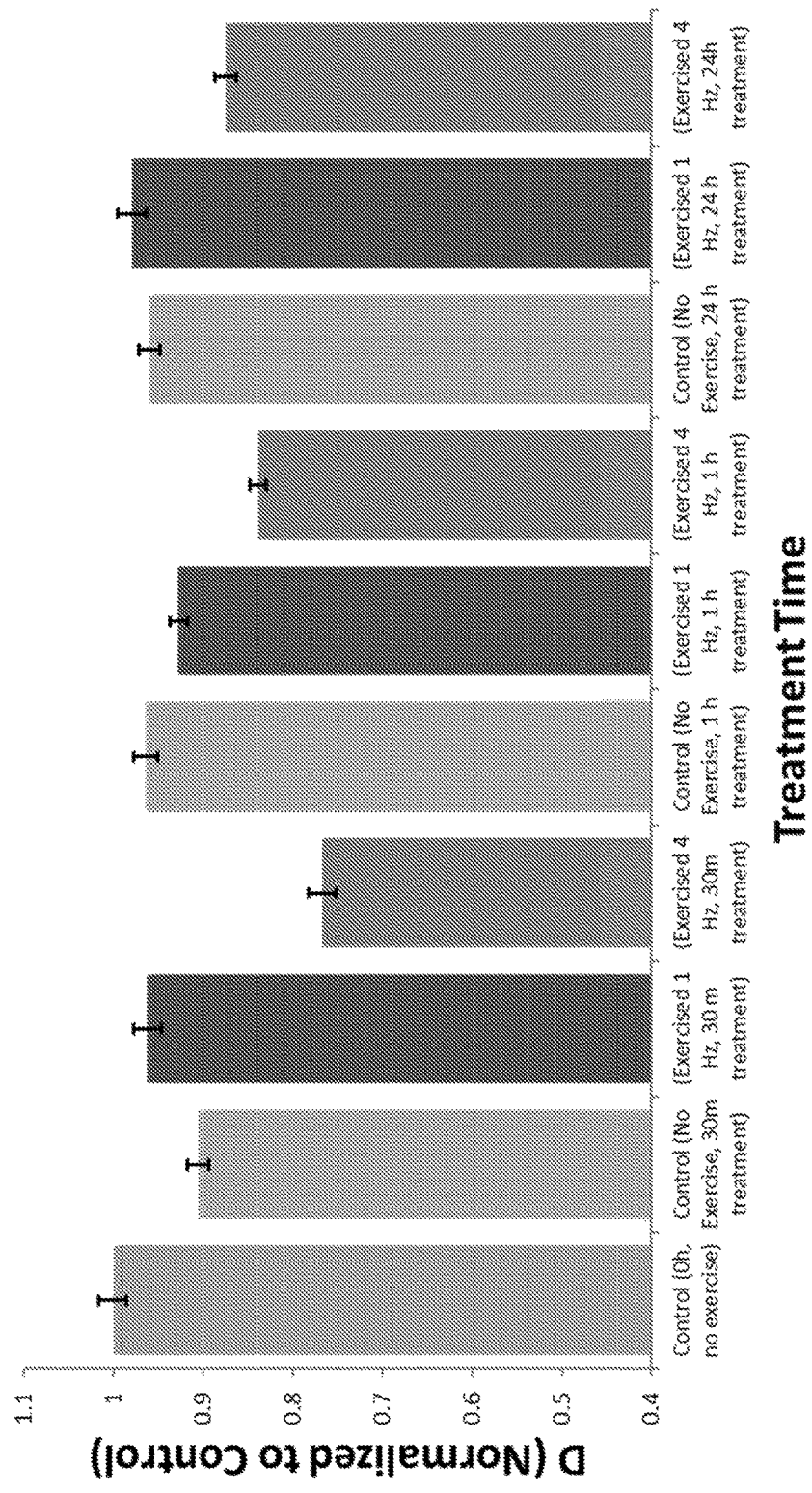
Figure 5:
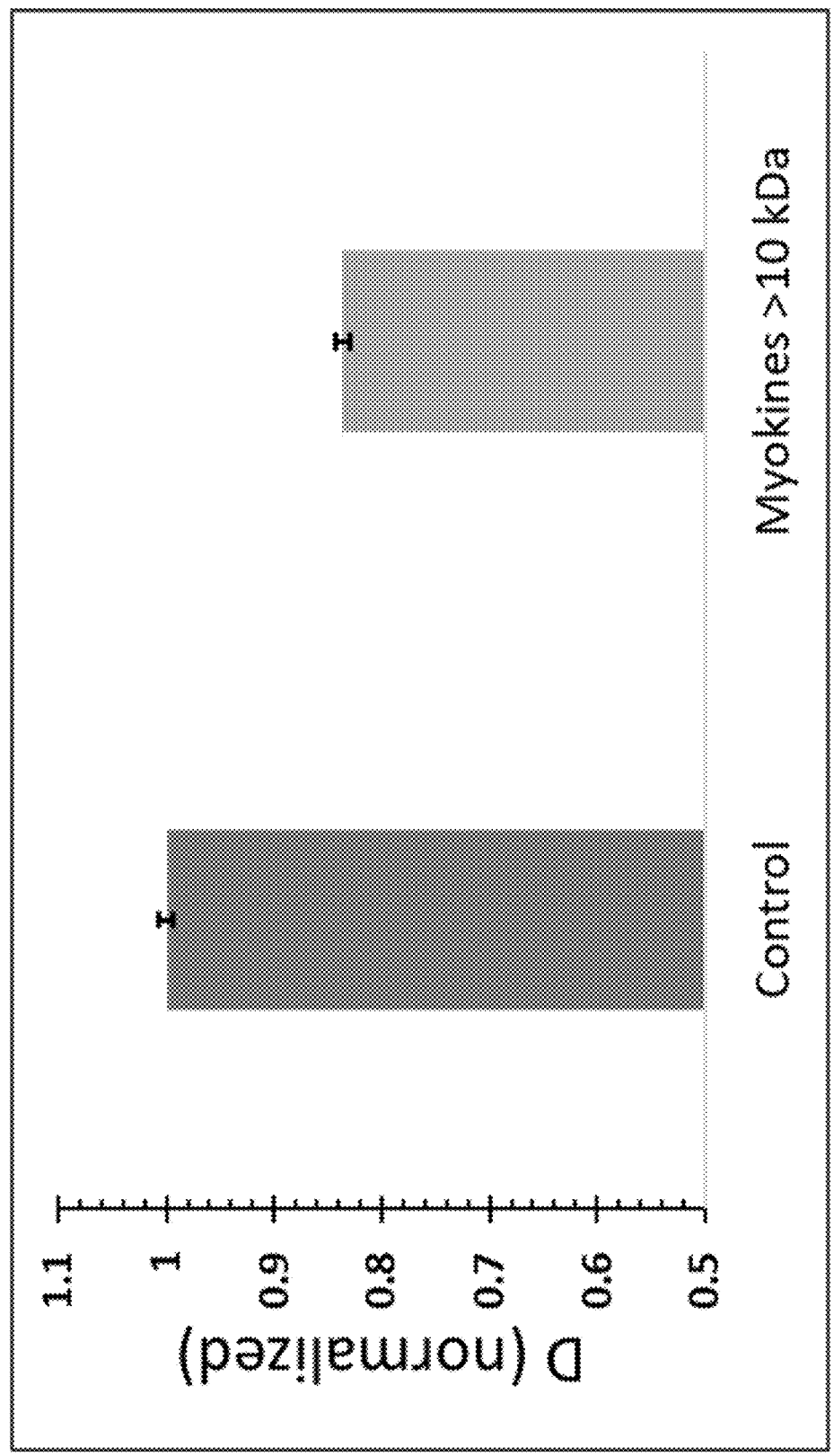

We next sought out to optimize condition for producing stimulated media which modulates chromatin density (D) in colorectal cells. (See FIG. 5). In particular, we varied conditions under electrical pulse stimulation (EPS), including stimulation time, potential (voltage (V)), and frequency (Hertz (Hz)). We also fractionated the myokine and observed that a fraction having a molecular weight greater than about 10 kDa modulated chromatin density.

Figure 6:
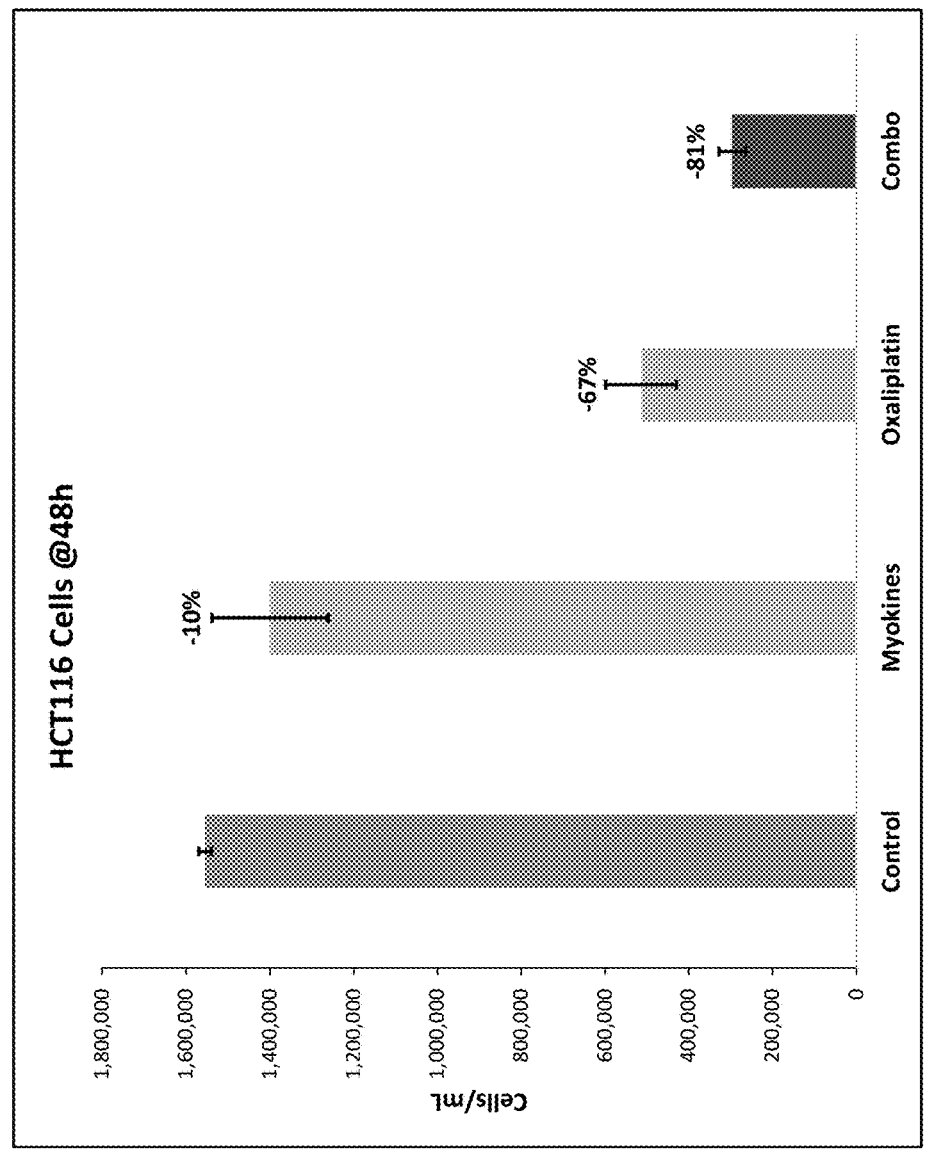
FIG. 6. Treatment of colon cancer cells lines with myokines and oxaliplatin. (a) HCT116 cells treated with myokines, oxaplatin, and combination of myokines and oxaplatin. (b) H29 cells treated with oxoplatin (ox), myostatin, and a combination of myostatin and oxaplatin. (c) H29 cells treated with oxoplatin (ox), metrnl, and a combination of metrnl and oxaplatin.
Figure 6:
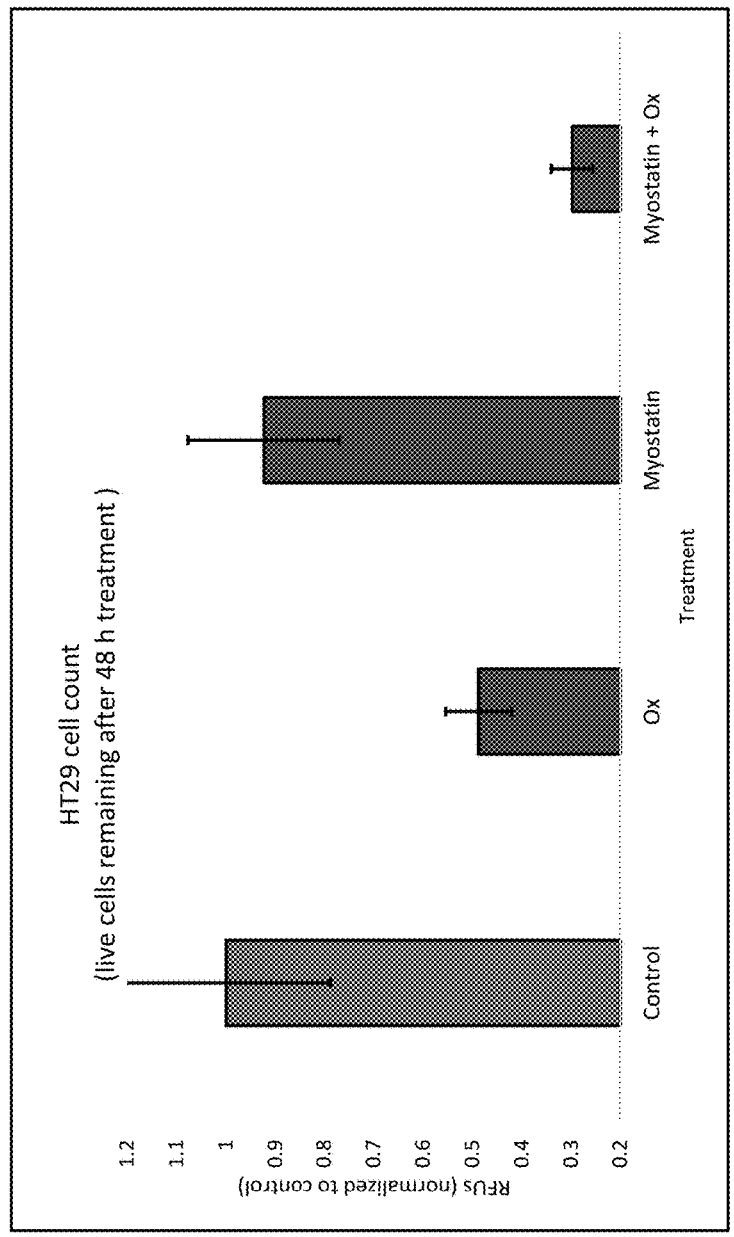
Figure 6:
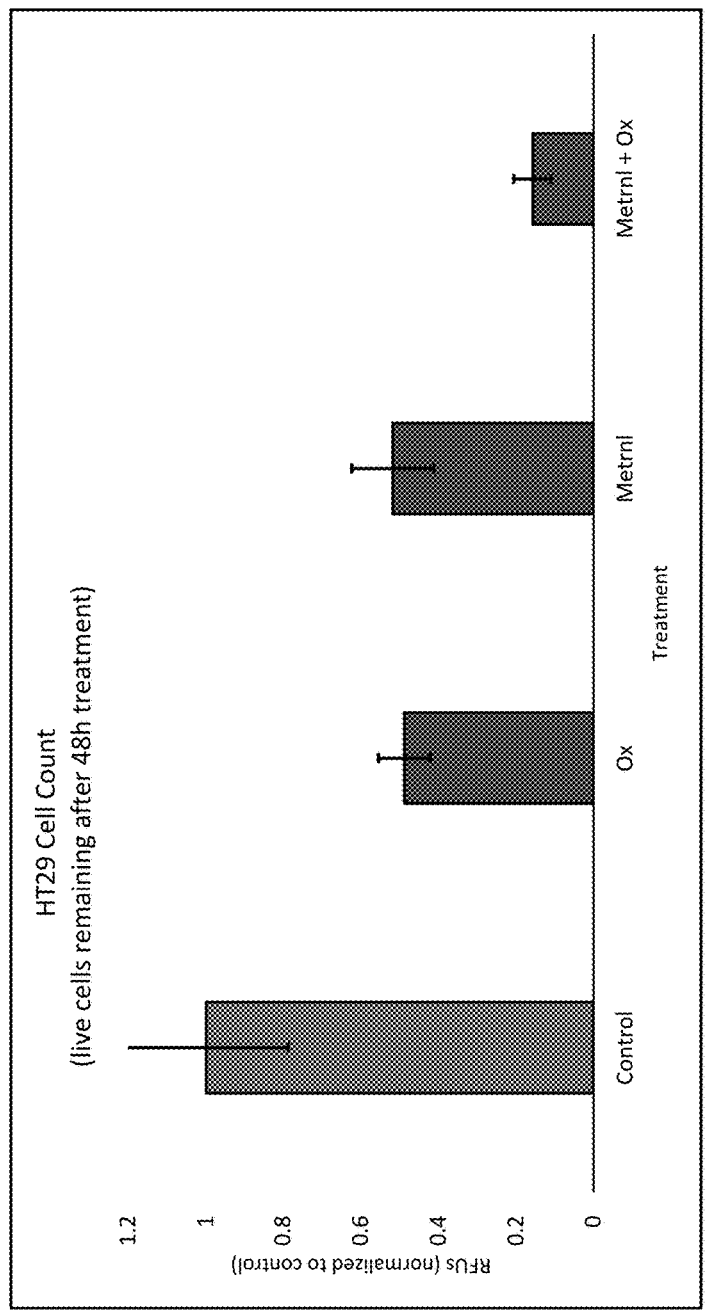

Next, we treated colorectal cancer cell lines HCT116 and HT29 with a myokine fraction and the specific myokines myostain and metrnl either by themselves or in combination with oxaliplatin. We observed that the myokine fraction and the specific myokines myostain and metrnl reduced the growth of the colorectal cancer cell lines and that there was a synergistic effect when the myokines were administered in combination with oxaliplatin. (See FIG. 6).

Figure 7:
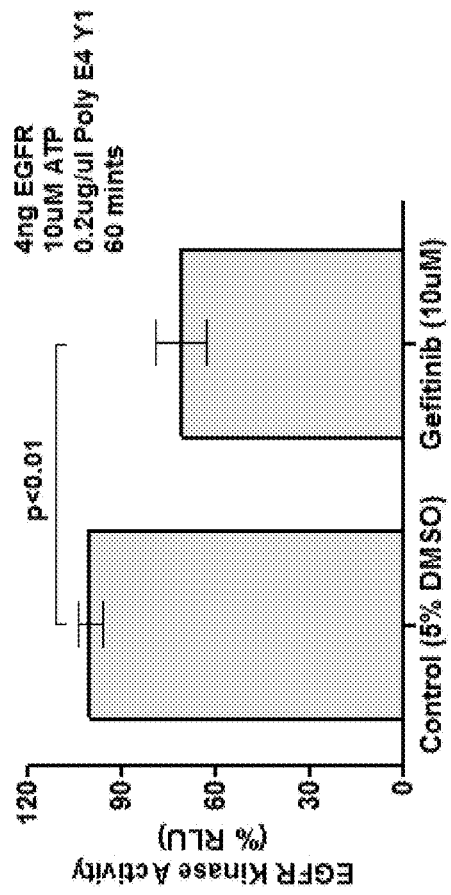
FIG. 7. Myokines modulate activity of epidermal growth factor receptor (EGFR). (a) stimulated myotubule media fraction having a molecular weight of greater than 10 kDa reduces kinase activity of purified EGFR. (b) reduction in chromatin density (D) after treatment with stimulated myotubule media and subsequent increase after EGFR is recycled to the cell membrane.
Figure 7:
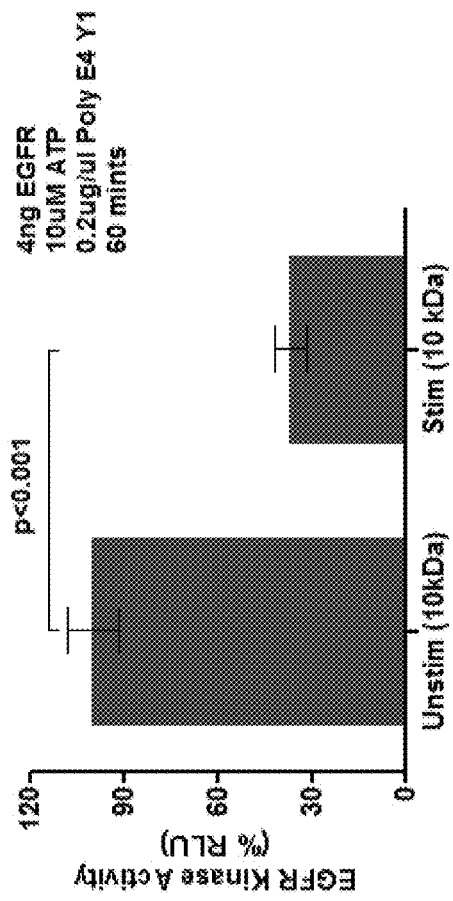
Figure 7:
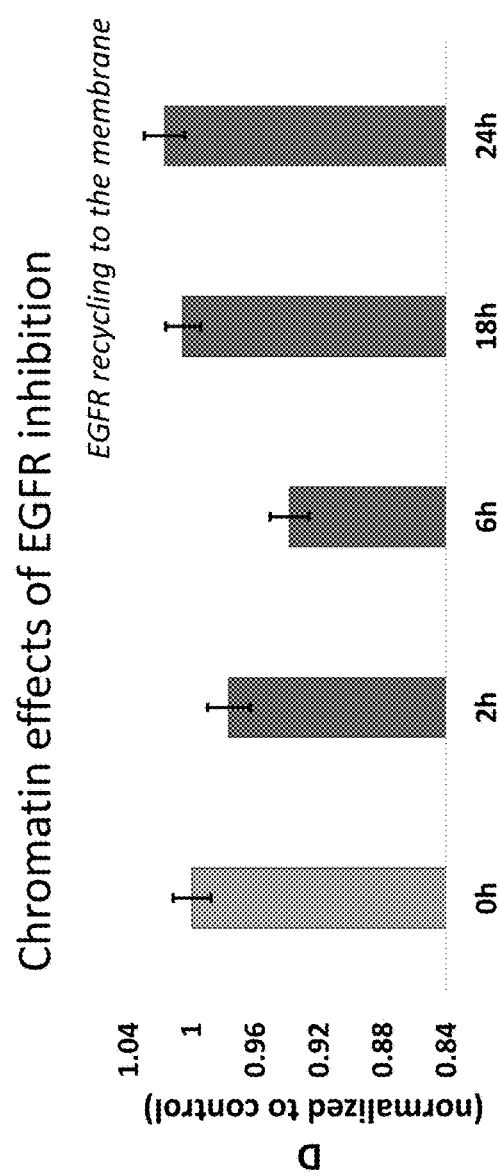
Figure 9:
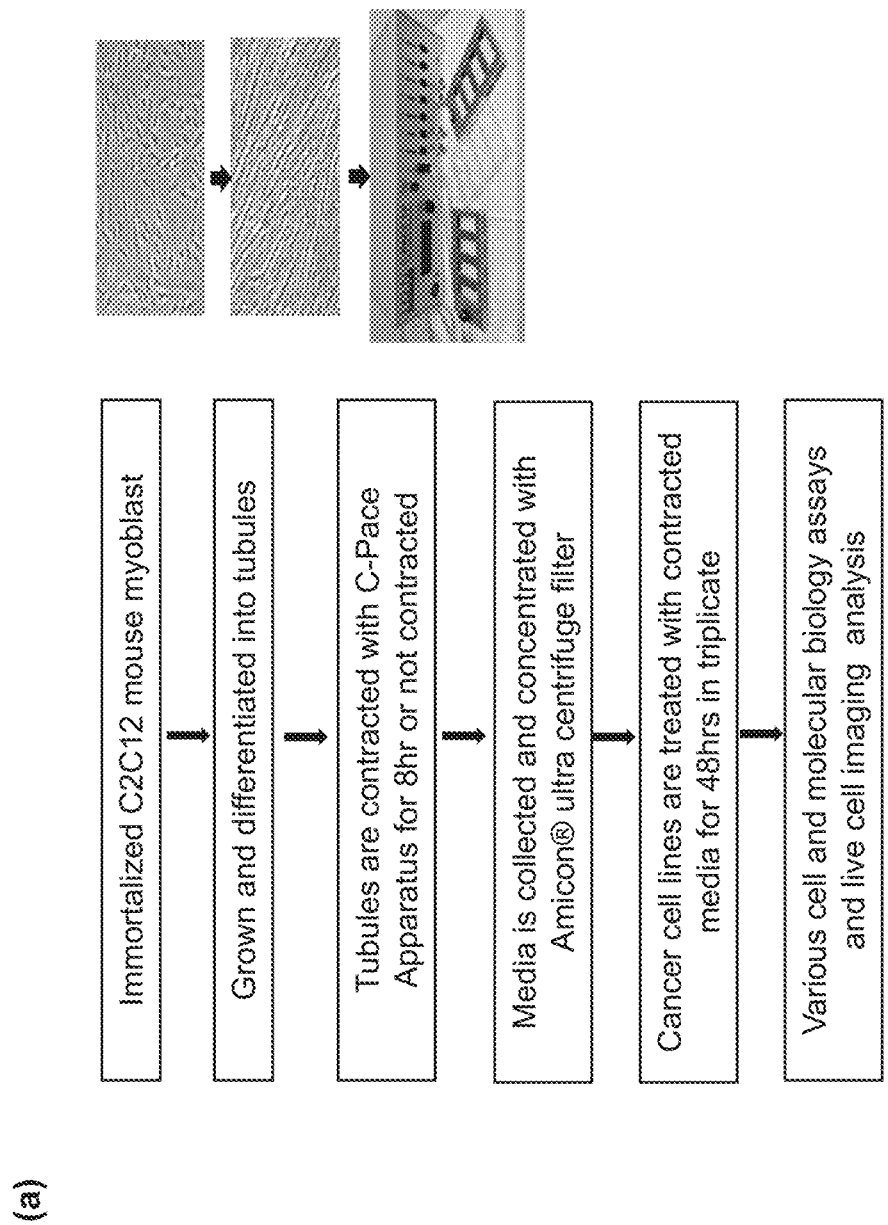
FIG. 9. Validation of in-vitro exercise model. (a) Flowchart for in vitro exercise model. (b) Mouse cytokine array—unstimulated and stimulated myokines. (c) Validation and quantification of myokines released following exercise stimulation using Milliplex® mouse myokine array.
Figure 9:
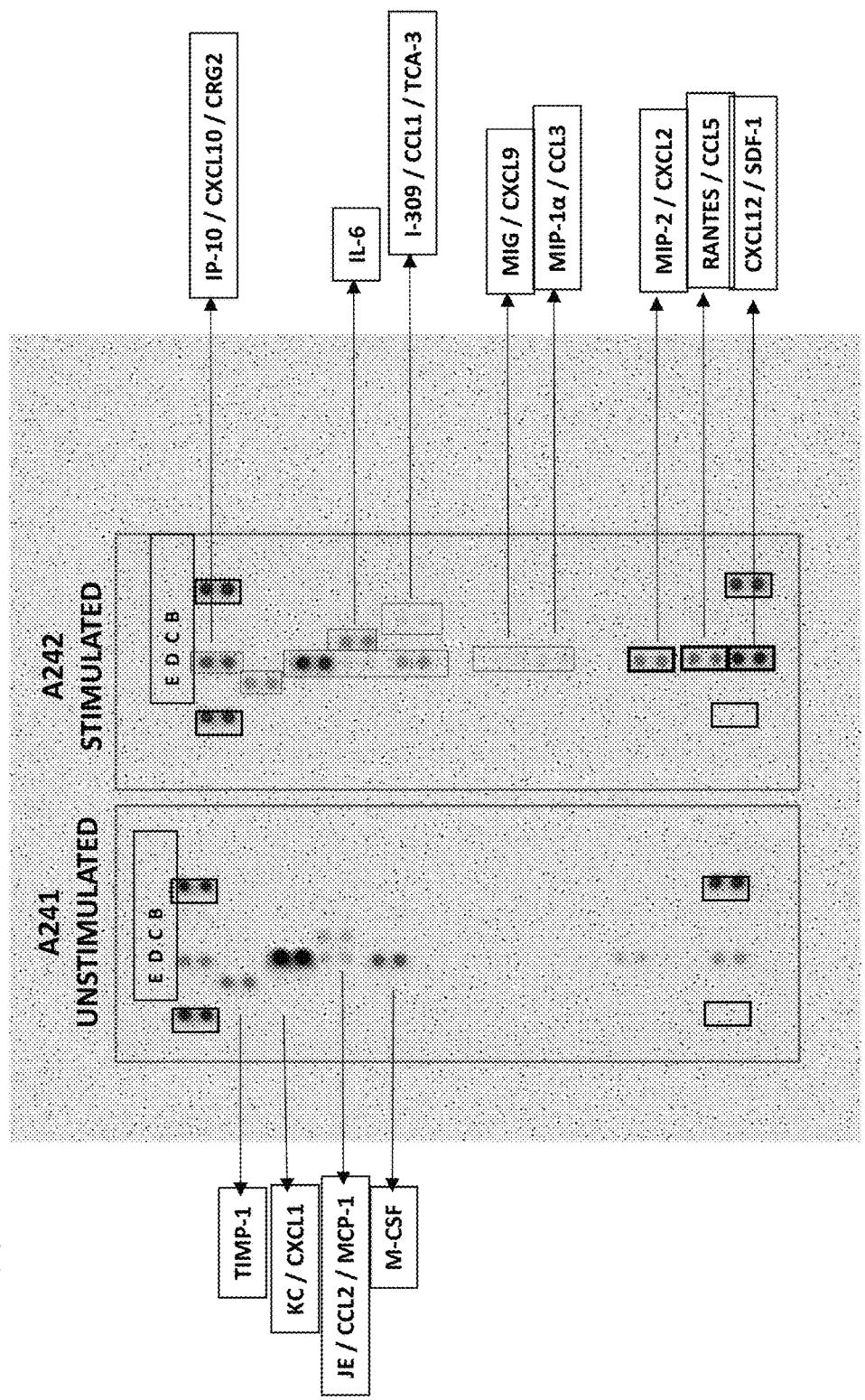
Figure 9:
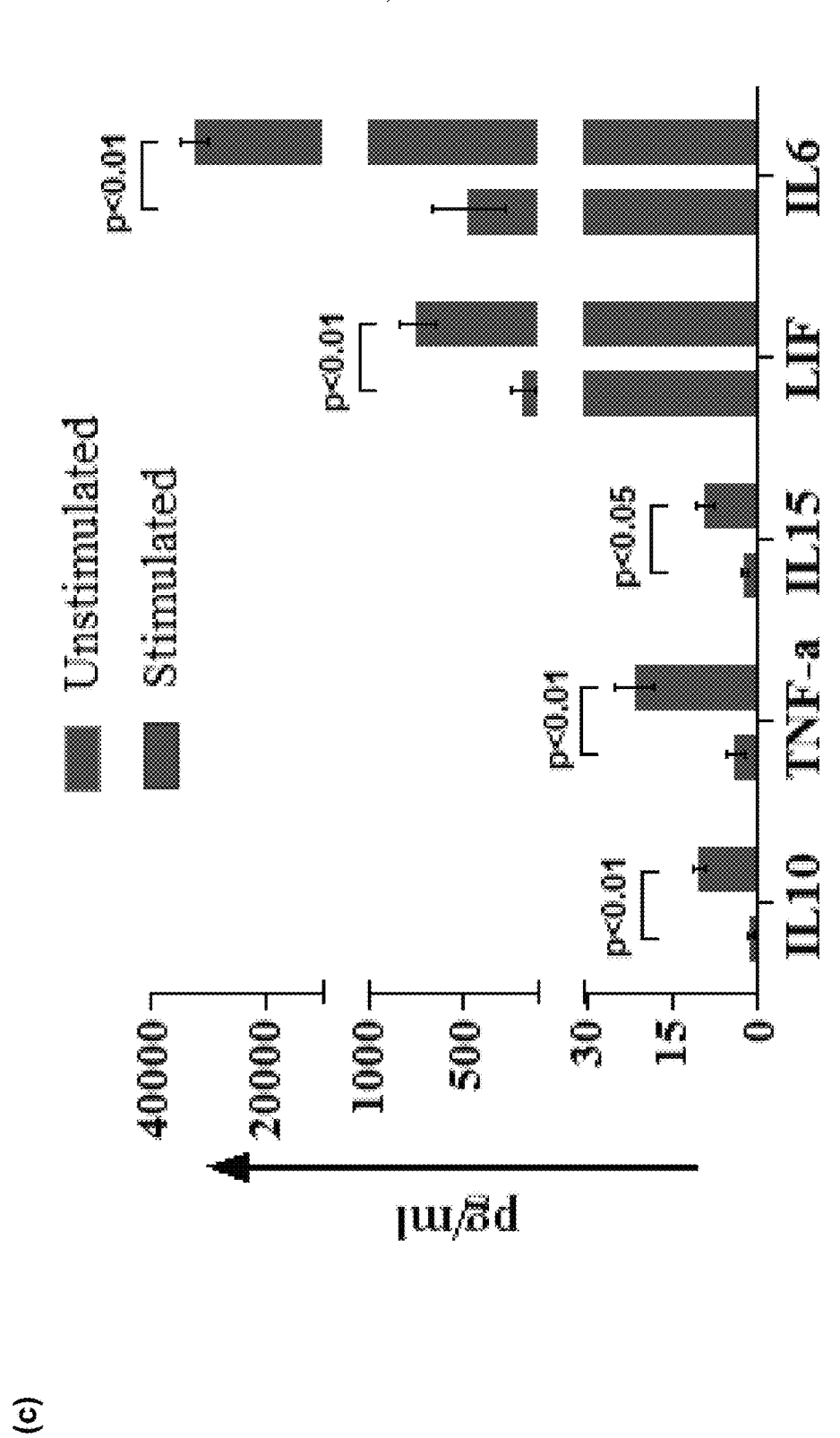
Figure 10:
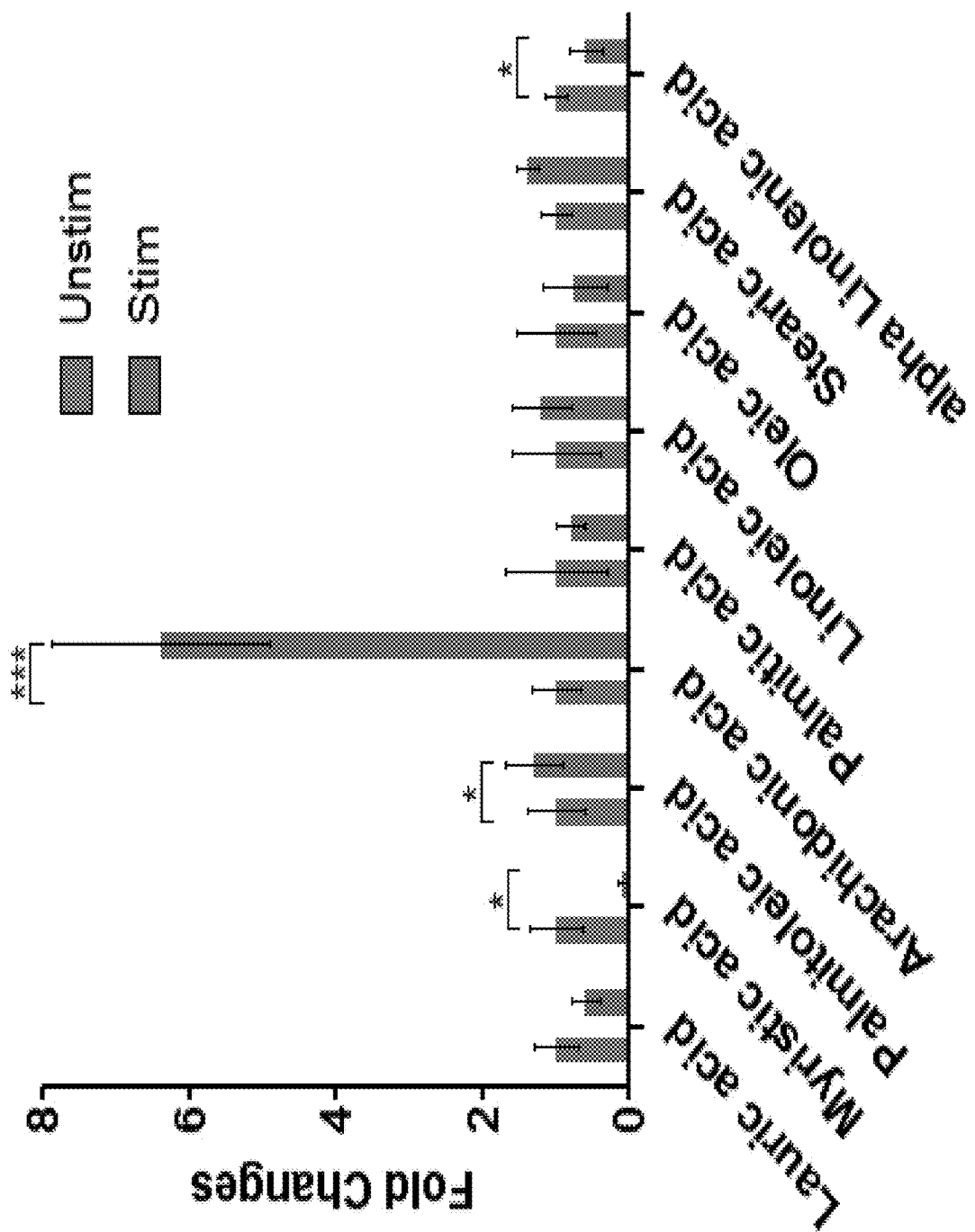
FIG. 10. Lipidomics analysis of HT29 CRC cells treated with exercise stimulated myokines. Differential level of several free fatty acids in HT29 cells treated with exercise stimulated media and unstimulated media control.
Figure 11:
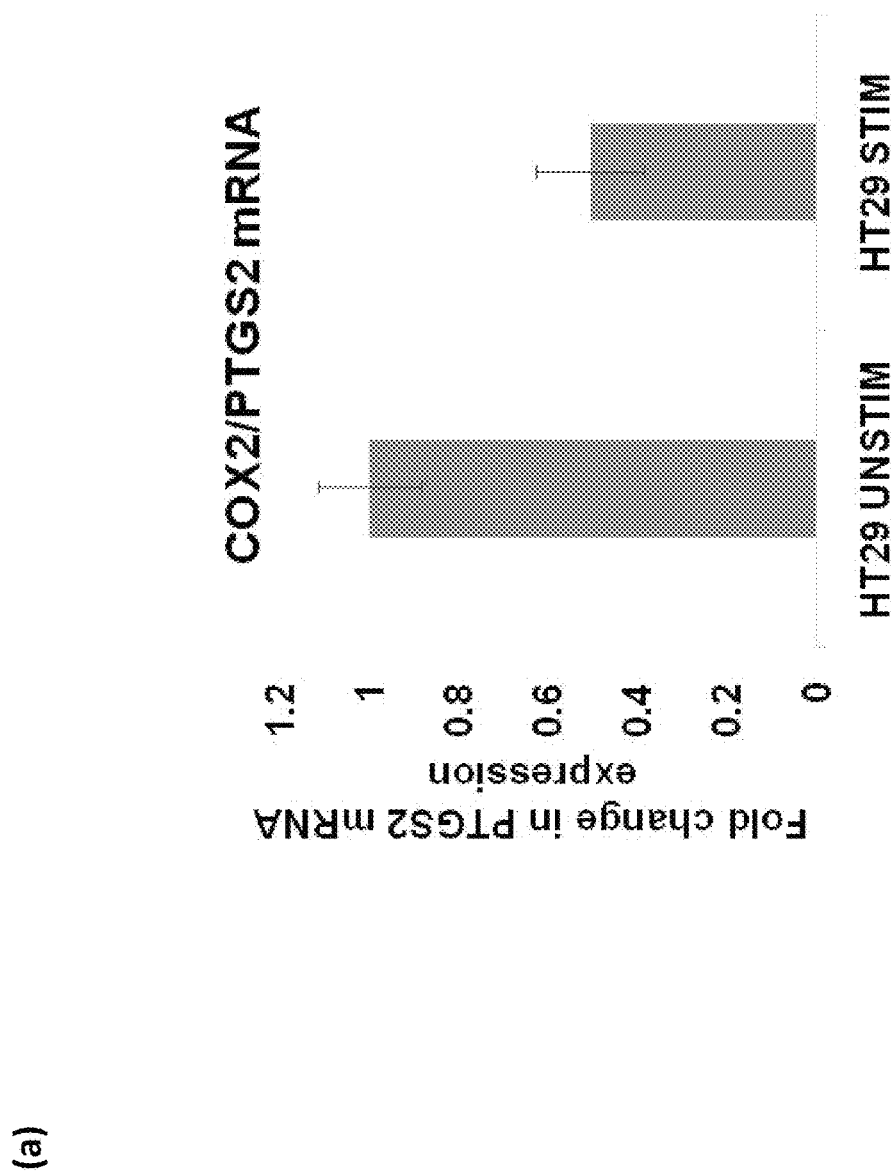
FIG. 11. Effect of exercise stimulated myokines on COX-2 gene expression and its downstream signaling pathway. (a) Relative mRNA expression of COX2 gene in HT29 cells 48 hrs post treatment with exercise stimulated media (STIM) and unstimulated media control (UNSTIM). (b) Relative luciferase assay using COX-2-promoter-reporter clone and secrete-pair dual luminescence assay kit (Genecopoeia #HPRM30889-PG04 and LF031 respectively). (c) Measurement of PGE2 level using Prostaglandin E2 Express ELISA kit (Cayman Chemical; #500141) in HT29 cells 48 hrs post treatment. (d,e) Relative luciferase assay in HT29 cells 48 hrs post treatment with different molecular weight fractions of exercise stimulated media and unstimulated media controls.
Figure 11:
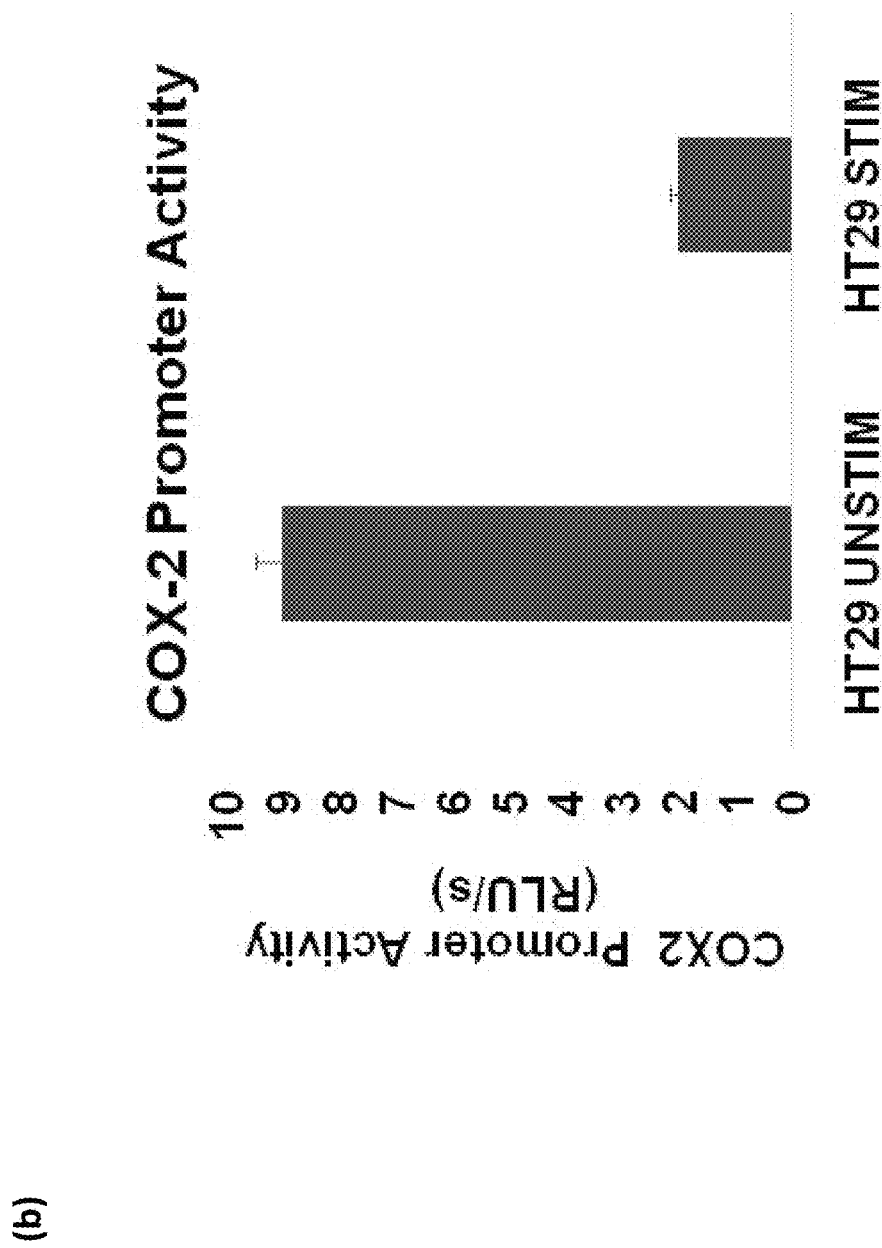
Figure 11:
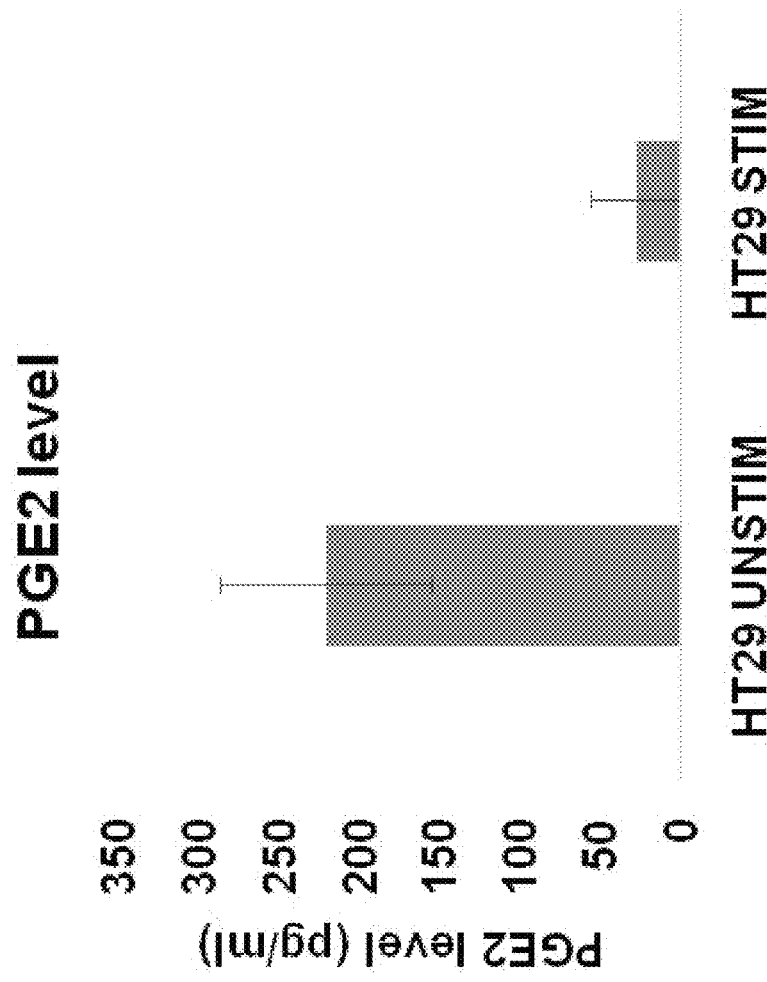
Figure 11:
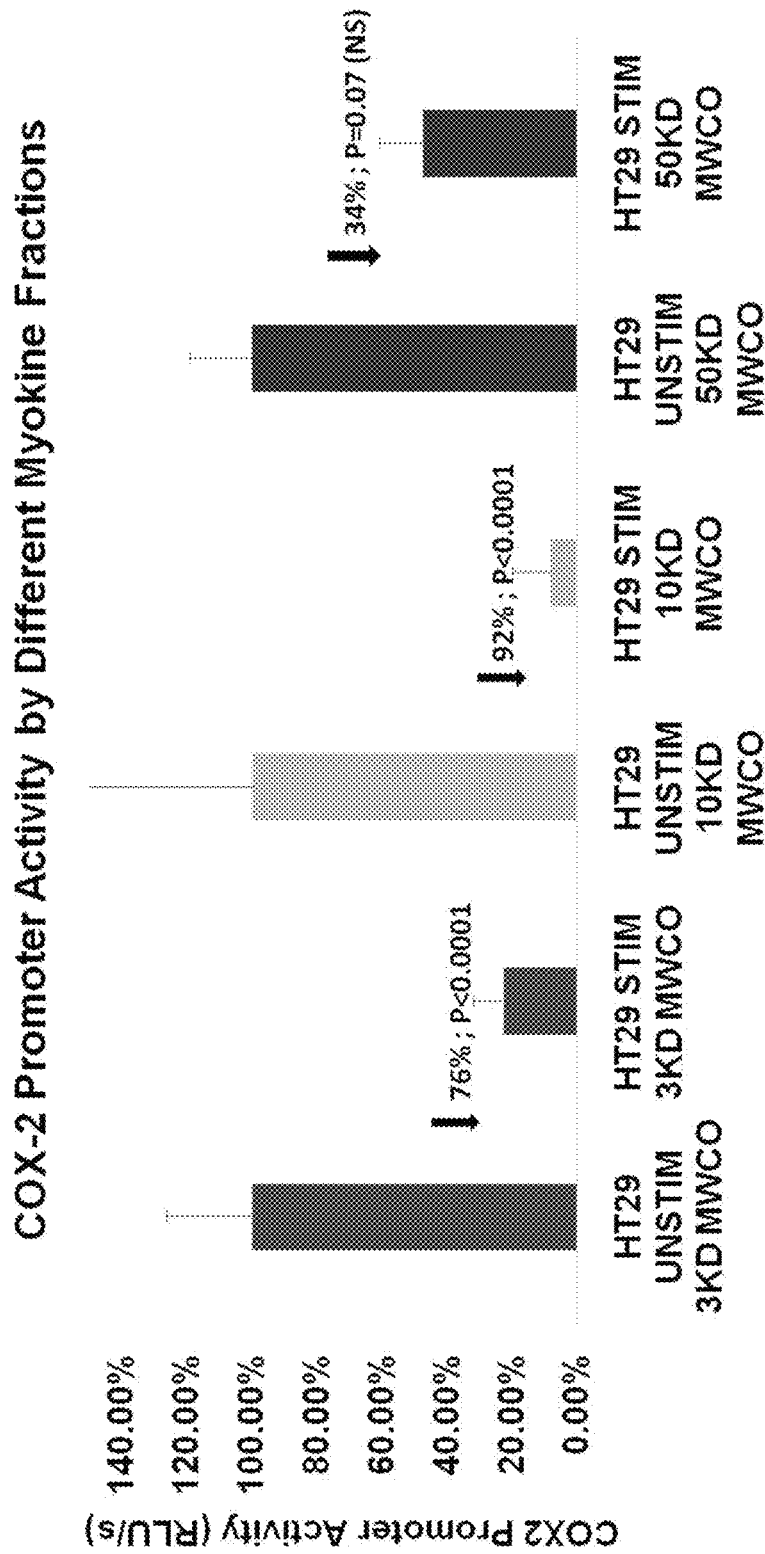
Figure 11:
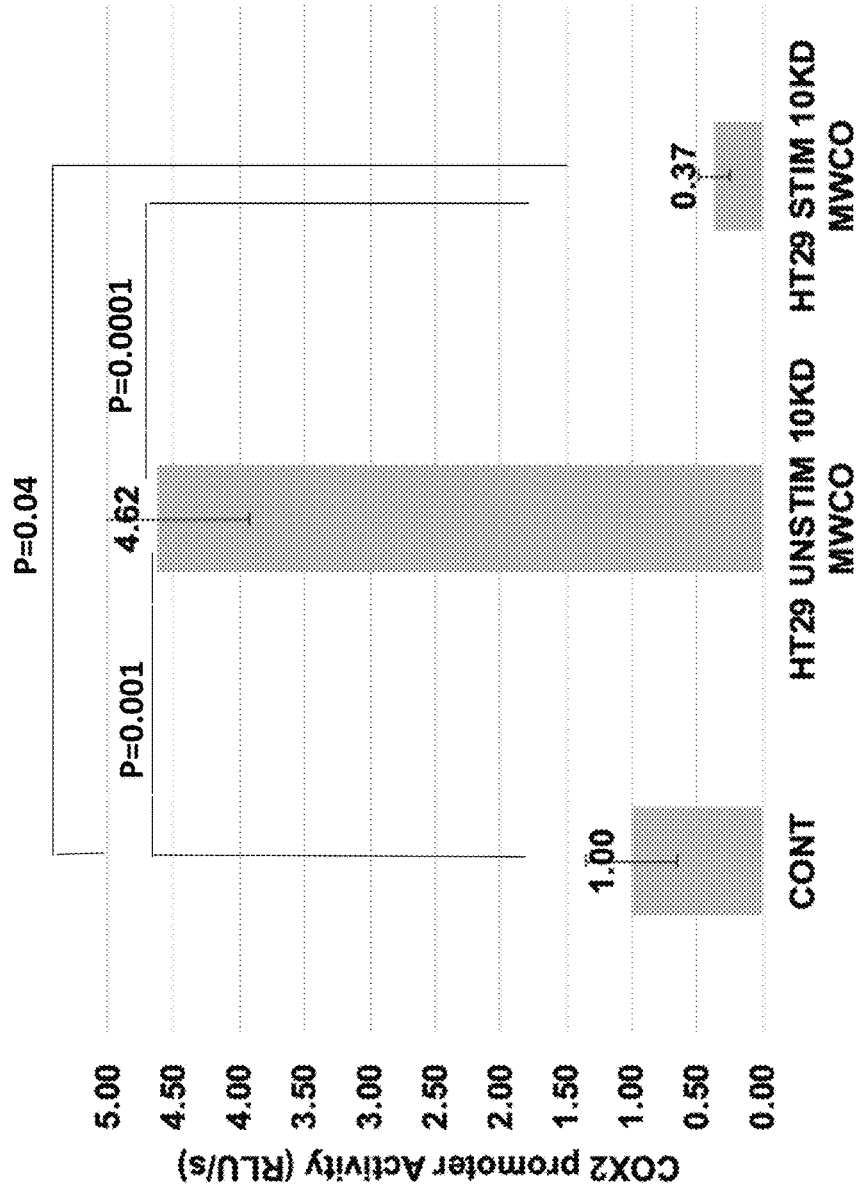
Figure 12:
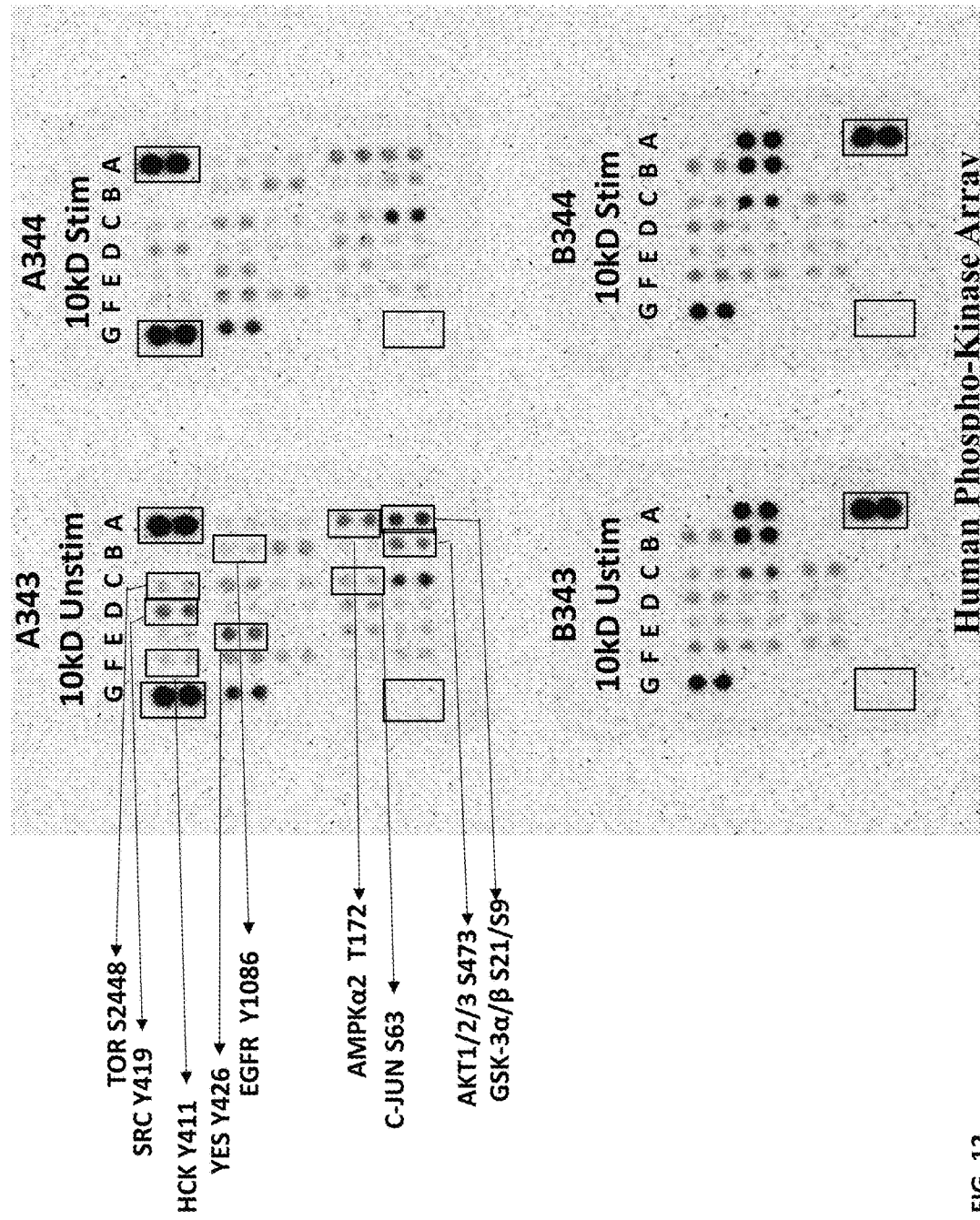
FIG. 12. Exercise stimulated myokine fraction predominantly targets COX-2 and EGFR signaling pathway to inhibit cellular proliferation. The relative levels of phosphorylation of different kinases, transcription factors and receptor tyrosine kinases (RTKs) were determined in HT29 cells 48 hrs post treatment with exercise stimulated 10 kD fraction (10 kD STIM) and unstimulated media control (10 kD UNSTIM) using Human Phospho-kinase Array Kit (a,b) and Human Phospho-RTK Array Kit (R&D Systems, MN) (c,d). WST assay was performed using HT29 cells 48 hrs post treatment with combination of celecoxib (75 uM, COX2 inhibitor), gefitinib (10 uM, EGFR inhibitor) and 10 kD myokine fraction (e).
Figure 12:
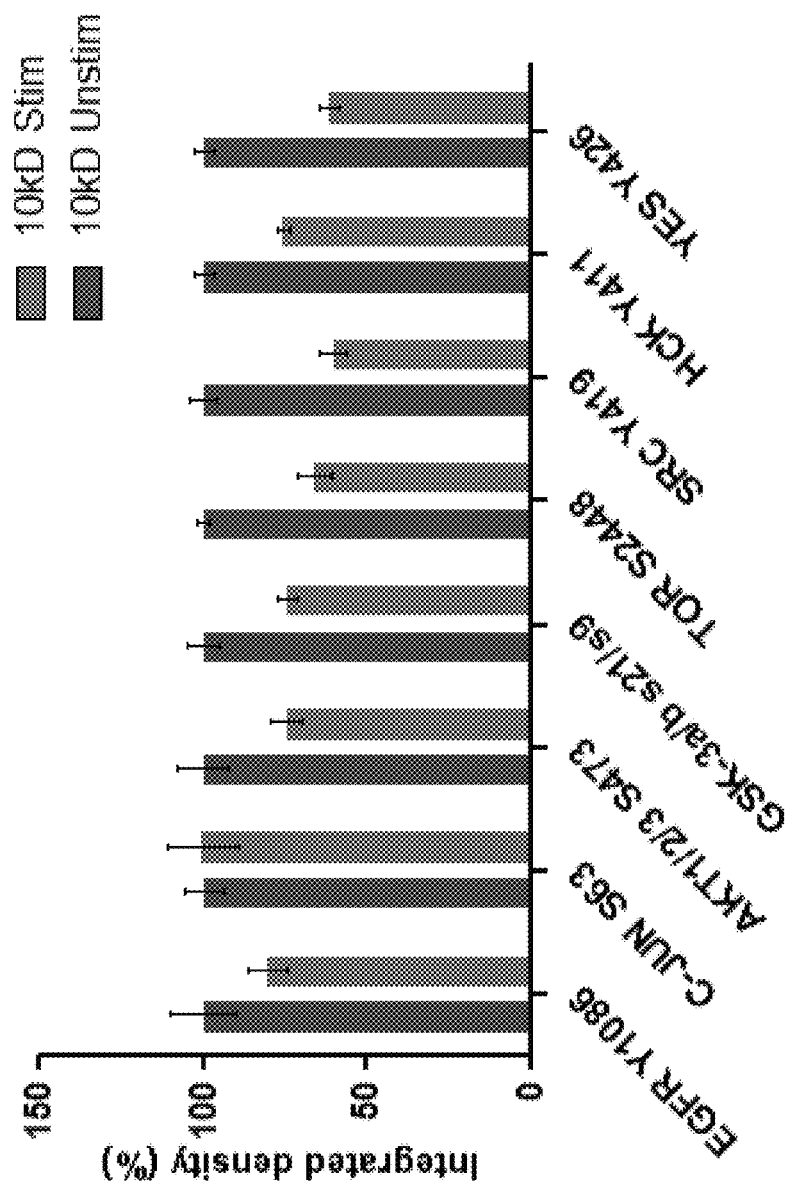
Figure 12:
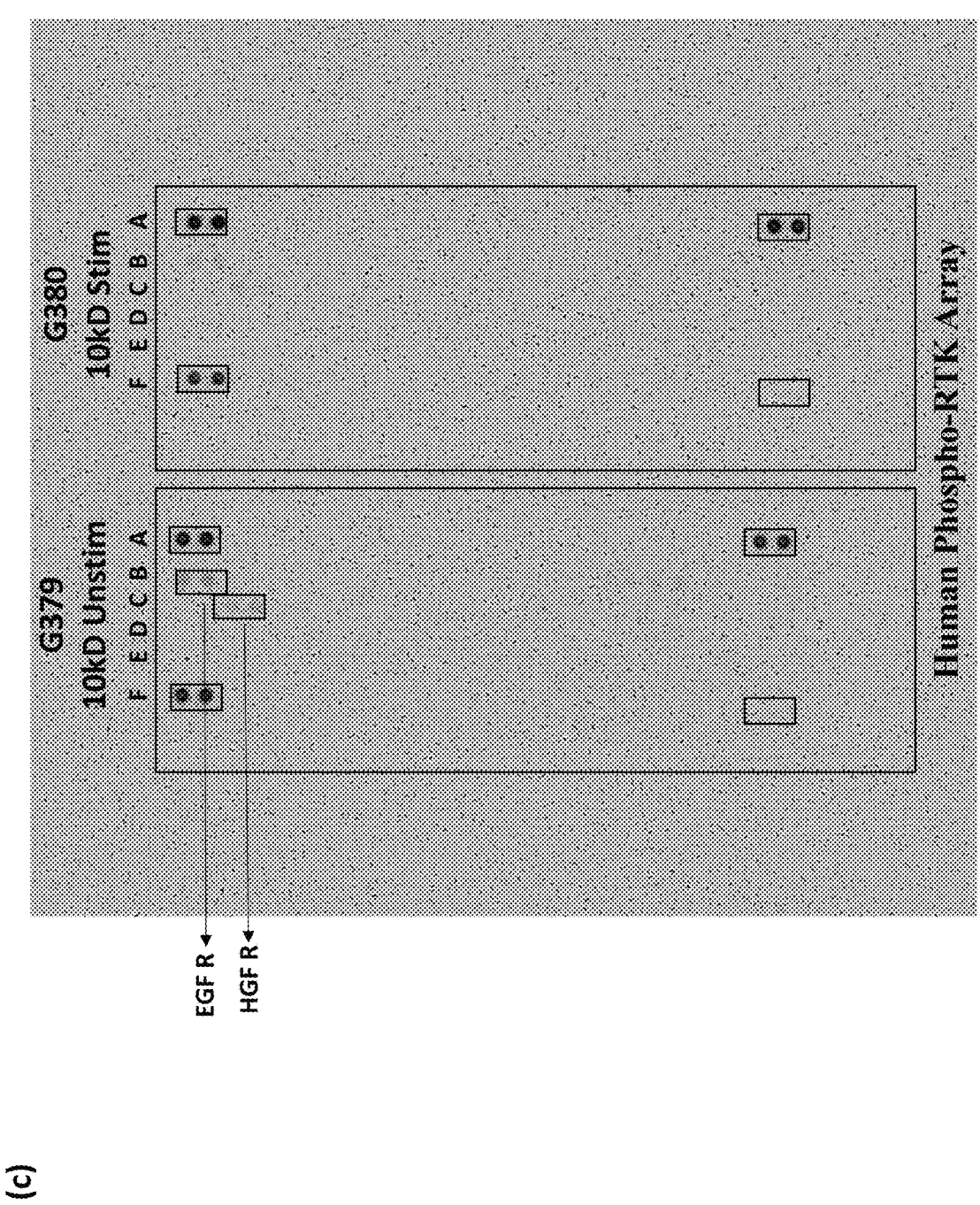
Figure 12:
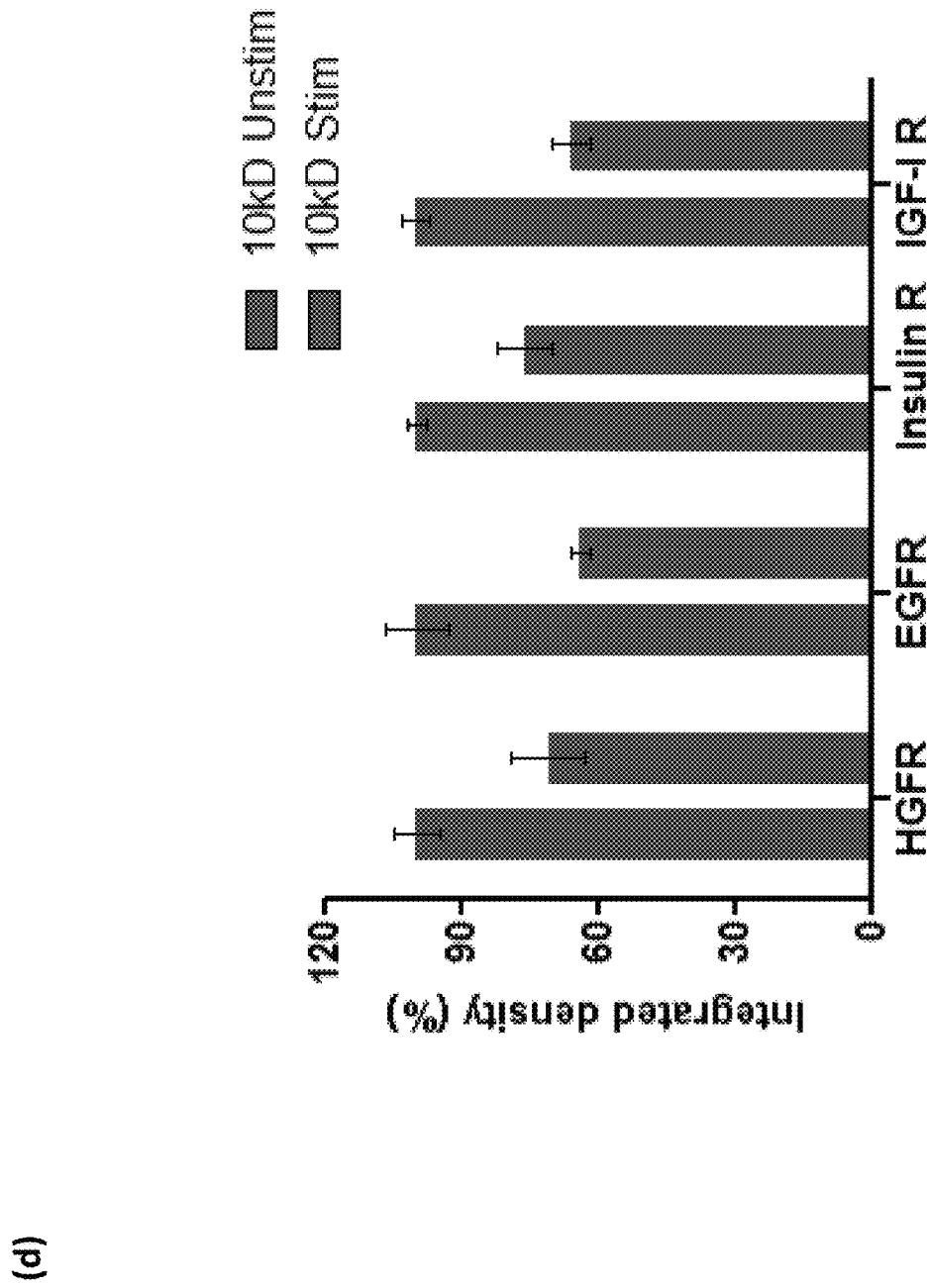
Figure 12:
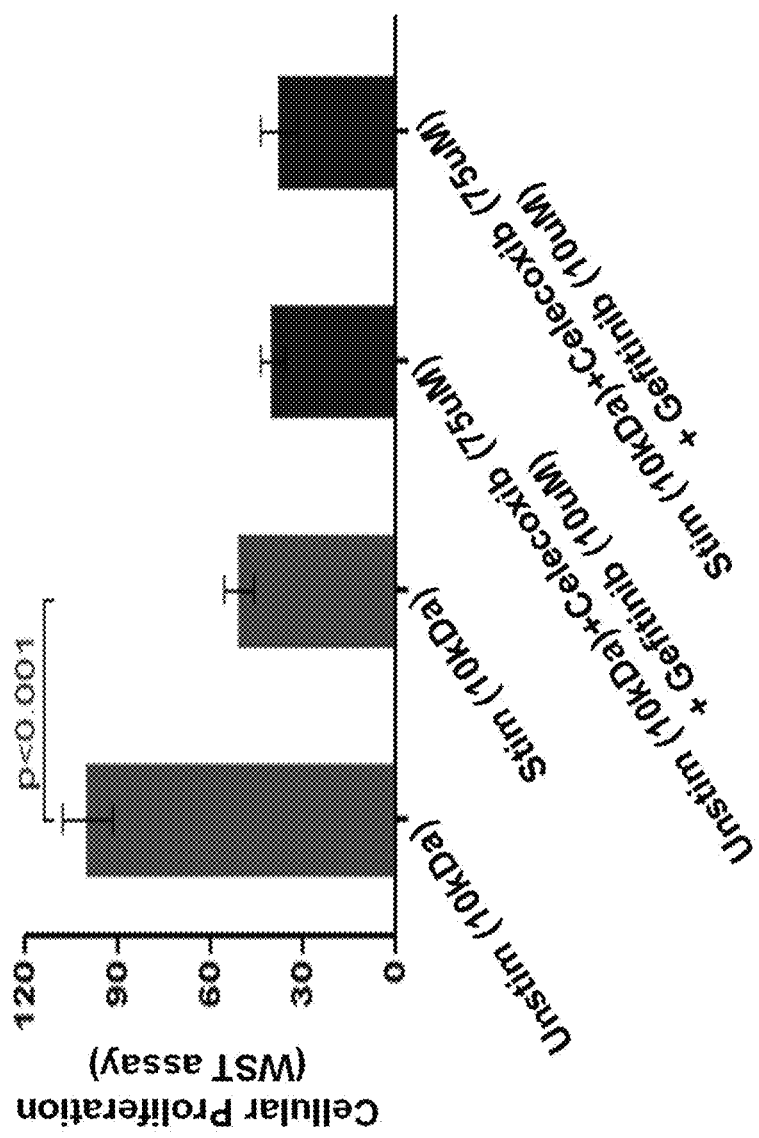

We also used the Phospho-RTK Array Kit (R&D Systems, MN) to evaluate whether the biological activity of any particular proteins were downregulated by exercise stimulation. We identified several receptor tyrosine kinases whose biological activity was downregulated by exercise stimulation, and those four having the most downregulated activity included EGFR (epidermal growth factor receptor), HGFR (hepatocyte growth factor receptor) insulin receptor and IGF-1 R (insulin growth factor one receptor). (Data not shown). Given that EGFR is an established target for anti-cancer therapies, we focused on identifying myokines that target EGFR. We utilized an in vitro system with exogeneous purified EGFR and noted that simply adding the 10 kDa myokine fraction that we isolated from our system suppressed EGFR activity using a commercially available activity assay and that the suppression of activity was equivalent or greater than that with the small molecule inhibitor gefitinib. (See FIG. 7($a$)). In addition, we observed a reduction in chromatin density (D) after treatment with stimulated myotubule media and a subsequent increase after EGFR was recycled to the cell membrane. (See FIG. 7($b$)). This shows, for the first time, that myokines directly interact with EGFR (and potentially other receptor tyrosine kinases) to suppress activity of these proto-oncogenes.

There are a number of chemotherapeutic agents that target EGFR for treating EGFR-dependent cancers. (See FIG. 8). However, many of these anti-EGFR agents have toxic, off-target effects. Our results suggest that one or more components of the myokinome may be administered instead of these anti-EGFR agents. Alternatively, one or components of the kinome (i.e., one or more myokines) may be administered in conjunction with these anti-EGFR agents where the anti-EGFR agents may be administered at a dose that is sub-therapeutic and non-toxic when the anti-EGFR agents are administered alone, but therapeutic when the anti-EGFR agents are administered with the one or more components of the kinome.

Although the total myokinome has chromatin-normalizing effects and reduces phenotypic plasticity of cancer cells, which in turn translates into anti-neoplastic properties, certain individual myokines or their specific combinations may have the opposite effect and may increase phenotypic plasticity. These myokines would be of potential interest to address processes where increased transcriptional adaptability is beneficial. Examples include cell adaptation to stressors such as ischemia (e.g. limiting neuronal or myocardial damage in patients with stroke or myocardial ischemia, respectively). The experimental proof remains to be developed.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A kit for treating colorectal cancer, the kit comprising: (a) a first pharmaceutical composition comprising an isolated fraction of myokines comprising an effective amount of one or more myokines for treating colorectal cancer, wherein (i) the one or more myokines have a molecular weight greater than about 10 kDa; and/or (ii) the one or more myokines comprise myostatin, metrnl, or both of myostatin and metrnl; and (b) a second pharmaceutical composition comprising an effective amount of a platinum-based chemotherapeutic agent for treating colorectal cancer.

2. The kit of claim 1, wherein the isolated fraction of myokines comprises an effective amount of one or more myokines for treating a colorectal cancer whose growth is associated with chromatin density.

3. The kit of claim 1, wherein the isolated fraction of myokines comprises an effective amount of one or more myokines for treating a cancer whose growth is associated with epidermal growth factor receptor (EGRF) activity.

4. The kit of claim 1, wherein the isolated fraction of myokines comprises an effective amount of one or more myokines for inhibiting epidermal growth factor receptor (EGRF) activity.

5. The kit of claim 1, wherein the kit first pharmaceutical composition comprises myostatin.

6. The kit of claim 1, wherein the first pharmaceutical composition comprises myostatin and the second pharmaceutical composition comprises oxaliplatin.

7. The kit of claim 1, wherein the first pharmaceutical composition comprises metrnl.

8. The kit of claim 1, wherein the first pharmaceutical composition comprises metrnl and the second pharmaceutical composition comprises oxaliplatin.

9. A method for treating colorectal cancer in a subject in need thereof, the method comprising administering to the subject the first pharmaceutical composition and the second pharmaceutical composition of the kit of claim 1.

* * * * *

UNITED STATES PATENT AND TRADEMARK OFFICE
CERTIFICATE OF CORRECTION

PATENT NO. : 11,560,414 B2
APPLICATION NO. : 16/877275
DATED : January 24, 2023
INVENTOR(S) : Hemant K. Roy et al.

It is certified that error appears in the above-identified patent and that said Letters Patent is hereby corrected as shown below:

In the Specification

Column 2, Line 32, "(0)" should be --(O)--.

In the Claims

Column 18, Line 22, Claim 5, "the kit first" should be --the first--.

Signed and Sealed this
Eleventh Day of April, 2023

Katherine Kelly Vidal
*Director of the United States Patent and Trademark Office*